United States Patent [19]

Bruchman et al.

[11] Patent Number: 5,762,600

[45] Date of Patent: Jun. 9, 1998

[54] BLOOD CONTACT SURFACES EMPLOYING NATURAL SUBENDOTHELIAL MATRIX AND METHODS FOR MAKING AND USING THE SAME

[75] Inventors: William Carl Bruchman, Flagstaff; Anita Jean Switzer, Parks, both of Ariz.

[73] Assignee: W. L. Gore & Associates, Inc., Newark, Del.

[21] Appl. No.: 665,596

[22] Filed: Jun. 18, 1996

Related U.S. Application Data

[63] Continuation of Ser. No. 424,698, Apr. 19, 1995, abandoned, which is a continuation-in-part of Ser. No. 235,045, Apr. 29, 1994, abandoned.

[51] Int. Cl.$^6$ ............................................. A61F 2/04
[52] U.S. Cl. .................................. 600/36; 623/1; 623/12
[58] Field of Search ........................... 623/1, 11, 12; 600/36

[56] References Cited

U.S. PATENT DOCUMENTS

| | | |
|---|---|---|
| 2,900,644 | 8/1959 | Rosenberg et al. |
| 3,927,422 | 12/1975 | Sawyer. |
| 3,953,566 | 4/1976 | Gore. |
| 3,988,782 | 11/1976 | Dardik et al. |
| 4,083,066 | 4/1978 | Schmitz et al. |
| 4,098,571 | 7/1978 | Miyata et al. ............... 8/94.11 |
| 4,187,390 | 2/1980 | Gore. |
| 4,323,358 | 4/1982 | Lentz et al. |
| 4,383,832 | 5/1983 | Fraefel et al. |
| 4,539,716 | 9/1985 | Bell. |
| 4,546,500 | 10/1985 | Bell. |
| 4,553,974 | 11/1985 | Dewanjee ................... 8/94.11 |
| 4,671,797 | 6/1987 | Pedero. |
| 4,776,853 | 10/1988 | Klement et al. |
| 4,801,299 | 1/1989 | Brendel et al. ............... 623/1 |
| 4,804,381 | 2/1989 | Turina et al. |
| 4,804,382 | 2/1989 | Turina et al. |
| 4,883,755 | 11/1989 | Carabasi et al. |
| 4,960,423 | 10/1990 | Smith. |
| 5,037,378 | 8/1991 | Muller et al. |
| 5,131,908 | 7/1992 | Dardik et al. ................ 600/36 |
| 5,192,311 | 3/1993 | King et al. ................... 623/1 |
| 5,632,778 | 5/1997 | Goldstein .................... 623/11 |

OTHER PUBLICATIONS

J. A. Madri, et al., "The Collagenous Components of the Subendothelium," *Laboratory Investigations* 43:303-315 (1980).

T. Matsuda et al. "A Hybrid Artificial Vascular Graft Based upon an Organ Reconstruction Model: Significance and Design Criteria of an Artificial Basement Membrane," *ASAIO Transactions* 34:640–643 (1988).

(List continued on next page.)

*Primary Examiner*—Paul B. Prebilic
*Attorney, Agent, or Firm*—Eric J. Sheets

[57] ABSTRACT

This invention relates to improved vascular prostheses derived from mammalian blood vessels. The prostheses are fabricated from arterial segments from which the donor endothelium has been removed. A key aspect of this invention is the preservation of the subendothelial extracellular matrix that will serve as the blood interface of the vascular prostheses. The vessel segments are treated to reduce the likelihood of calcification and fixed with a tissue preservative. This invention results in vascular prostheses that are particularly useful for small diameter applications, such as arterial replacement requiring a diameter of 6 mm or less.

62 Claims, 4 Drawing Sheets

OTHER PUBLICATIONS

L. A. Erickson, "Regulation of Vascular Fibrinolysis," *Blood Vessel Wall and Thrombosis* 1:222–233 (Ed., R. Machovich, CRC Press 1988).

R. G. Petty et al., "Endothelium—The Axis of Vascular Health and Disease," *Journal of the Royal College of Physicians, London* 23:92–102 (1989).

R. E. Scharf et al., "Thrombosis and Atherosclerosis: Regulatory Role of Interactions Among Blood Components and Endothelium," *Blut* 55:131–144 (1987).

T. R. Weber et al. "Viable Vein Graft Preservation," *Journal of Surgical Research* 18:247–255 (1975).

M. R. Buchanan et al., "The Basement Membrane Underlying the Vascular Endothelium Is Not Thrombogenic: In Vivo and In Vitro Studies with Rabbit and Human Tissue," *Thrombosis and Haemostasis* 58:698–704 (1987).

J.C. de Graaf et al., in their paper, "Platelet Adhesion to Subendothelial Structures Under Flow Conditions: No Effect of the Lipoxygenase Product 13–HODE," *Thrombosis and Haemostasis* 62:802–806 (1989).

J. Aznar–Salatti et al., "Platelet Adhesion to Exposed Endothelial Cells Extracellular Matrixes Is Influenced by the method of Preparation," *Arteriosclerosis and Thrombosis* 11:436–442 (1991).

M. Richardson et al., "Wound Healing in the Media of the Normolipemic Rabbit Carotid Artery Injured by Air Drying or by Balloon Catheter Deendothelialization" *American Journal of Pathology* 137:1453–1465 (1990).

M. A. Galumbeck et al., "Inhibition of Vessel Allograft Rejection by Endothelial Removal: Morphologic and Ultrastructural Changes," *Annals of Surgery* 206:757–764 (1987).

A. Albini et al., "Fibroblast Chemotaxis," *Collagen Related Research*, 5:283–296, (1985).

W. Morzycki et al., "Tumour Necrosis Factor–alpha but not Interleukin–1 induces Polymorphonuclear Leucocyte Migration through Fibroblast Layers by a Fibroblast–Dependent Mechanism," *Immunology*, 74:107–113 (1991).

BLOOD CONTACT SURFACES EMPLOYING NATURAL SUBENDOTHELIAL MATRIX AND METHODS FOR MAKING AND USING THE SAME

This a continuation application of application Ser. No. 08/424,698, filed Apr. 19, 1995 now abandoned, which is a continuation-in-part application of Ser. No. 08/235,045, filed Apr. 29, 1994, abandoned.

BACKGROUND OF THE INVENTION

1. Field of the Invention

The present invention relates to improved blood contact surfaces for use in apparatus such as artificial blood vessels and other implantable appliances, and methods for producing the blood contact surfaces.

2. Description of Related Art

The use of blood vessels taken from human or animal donors to replace blocked or damaged arteries has been widely practiced. Both fresh and preserved arterial allografts were extensively used as arterial substitutes in the 1950's. Although initial use appeared successful, allografts were largely abandoned by 1960 due to the high incidence of thrombosis, stenosis, and aneurysmal dilatation. Subsequent attempts to use vessels taken from other species have been similarly unsuccessful. Attempts have also been made to replace arteries with tissues of nonvascular origin, including autologous or xenogeneic fibrous tissue tubes, bovine ureter, and grafts made from small bowel and pericardium. However, like the above grafts from vascular sources, these nonvascular biological grafts have provided only very limited success.

Synthetic materials are also commonly used as blood vessel replacements. Synthetic vascular grafts first came into widespread use in the 1950's as a substitute for allograft transplantation. Synthetics were shown to be successful in the replacement of large vessels such as the aorta, iliac, or femoral arteries, and are still successfully employed in these applications. The principal synthetics used for this grafting are polyethylene terephthalate and expanded polytetrafluoroethylene (ePTFE). Unfortunately, like the biological grafts above, the performance of synthetics in demanding small diameter applications, such as coronary artery bypass or peripheral arterial bypass distal to the popliteal artery, has been substantially poorer than that of transplanted living autologous vessels.

The common surgical practice in the treatment of occlusive atherosclerotic disease of these smaller diameter arteries is to transplant a section of living vein, taken from the same individual, as a bypass around the occluded region of artery. However, approximately one fourth of all patients requiring peripheral arterial bypass have saphenous veins unsuitable for use because of varicosities, multi-branching, or inadequate diameter. These patients then require some alternative material with which the bypass can be effected. In addition, the transplanted vein itself is often susceptible to the atherosclerotic disease process. This atherosclerotic process is similar to that of the artery, but the vein is afflicted at an accelerated rate, frequently causing vein graft failure and necessitating an additional bypass. For these reasons, a need exists for a vascular substitute that would perform at least comparably to the autologous saphenous vein in the small diameter application.

In an attempt to provide alternatives to the use of saphenous veins, nonautologous vascular tissues have been employed as peripheral vascular substitutes. Some of these nonautologous tissues include fixed human umbilical vein, fixed bovine arteries, and cryopreserved human veins. For example, human umbilical cord arteries and veins are employed in U.S. Pat. No. 3,988,782, issued to Dardik et al., to produce allogeneic biological prostheses. This process involves placing the vessel over a mandrel for shaping followed by a hardening and glutaraldehyde fixation step to produce a graft of low antigenicity and thrombogenicity. A specific fixation process used to produce a xenogeneic bovine or porcine artery-based prostheses is described in U.S. Pat. No. 4,671,797, issued to Pedero. Pedero attempts to provide a xenogeneic arterial biological graft having structural and biological characteristics comparable to those of the recipient vessel. Bovine arteries, digested with proteolytic enzymes to produce tubes consisting largely of collagen, have also been used as nonautologous vascular grafts. U.S. Pat. Nos. 2,900,644, issued to Rosenberg et al.; 3,927,422, issued to Sawyer; 4,083,066, issued to Schmitz et al.; 4,098,571, issued to Miyata et al.; and 4,383,832, issued to Fraefel et al. describe such processing using the enzymes ficin, trypsin, or papain. Digested arterial grafts such as these were found to exhibit a high incidence of thrombotic failure when used for lower limb bypass procedures, however.

A number of patents and publications describe other types of chemical processing of vascular-source tissues for vessel replacement. For example, U.S. Pat. Nos. 4,323,358, issued to Lentz et al. and 4,553,974, issued to Dewanjee, disclose the use of detergents for the purpose of removing unwanted material and/or prevention of calcification. U.S. Pat. No. 4,801,299, issued to Brendel et al., describes a means by which tissues intended for implantation are prepared via sequential detergent treatments that extract cellular components leaving a sterile, nonantigenic, extracellular matrix implant composed largely of collagens. This process is said to provide implants with nonimmunogenicity and nonthrombogenicity that, when used for vascular replacements, provide high patency in grafts as small as 0.5 mm internal diameter. U.S. Pat. No. 4,776,853, issued to Klement et al., also employs a detergent extraction process similar to that disclosed in U.S. Pat. No. 4,801,299.

The precise mechanisms initiating and/or inhibiting thrombosis are of particular concern in attempts to develop artificial blood contact surfaces. Although a number of theories concerning the clotting mechanisms associated with blood contact materials have been advanced over the years, devices constructed in accordance with these theories have functioned only poorly in comparison to normal vasculature or empirically selected materials. The limited success achieved in the prior art has resulted from empirical attempts instead of mimicking the natural mechanisms of nonthrombogenicity.

Natural blood contact surfaces, such as those found within blood vessels, possess mechanisms to prevent thrombosis during normal passage of blood along the surface. In the case of a mammalian artery, the immediate blood contact surface is made of a layer of endothelial cells that is nonthrombogenic. Immediately external to the endothelial cell layer is the remainder of the intima: a subendothelial matrix composed of a basement membrane and underlying layer of glycoprotein-bearing extracellular matrix, and the internal elastic lamina. Surrounding the intimal layer is the multilaminate structure of the media containing smooth muscle cells and elastin, and surrounding this media, the most external layer composed of fibroblasts and connective tissue, the adventitia. As explained in greater detail below, it is generally accepted that the subendothelial matrix layer and media structures are thrombogenic in nature in order to maintain hemostasis when the vascular system is injured. See for example: J. A. Madri, et al., "The Collagenous Components of the Subendothelium," *Laboratory Investigations* 43: 303–315 (1980); and T. Matsuda et al. "A Hybrid Artificial Vascular Graft Based upon an Organ Reconstruction Model: Significance and Design Criteria of an Artificial Basement Membrane," *ASAIO Transactions* 34: 640–643 (1988).

Although the understanding of vessel wall architecture and biochemistry has grown significantly over the past decade, knowledge of the detailed mechanisms by which natural vessels maintain function has been very limited. The predominate theory relating to the effective function of normal vasculature is based upon the necessity of an intact vascular endothelium. The premise of this theory is that blood must interface only with healthy, intact endothelium or thrombosis will result. This assumption follows from numerous experiments showing that the endothelium has a unique clot-inhibiting effect on blood with which it is in contact. Endothelial cells have been shown to synthesize or bind a number of substances with coagulation-inhibiting or fibrinolytic function, including heparan sulfate/antithrombin III, dermatan sulfate/heparin cofactor II, thrombomodulin/protein C/protein S, prostacyclin, and tissue-type plasminogen activator. In addition, numerous experiments have been conducted to demonstrate that removal of the endothelial lining exposes structures shown to be thrombogenic.

Based on these observations and the blood-contacting location of the endothelium in the vascular system, it has been widely accepted that the endothelium is primarily, if not wholly, responsible for the antithrombogenic behavior of blood vessels. See for example: L. A. Erickson, "Regulation of Vascular Fibrinolysis," *Blood Vessel Wall and Thrombosis* 1: 222–233 (Ed., R. Machovich, CRC Press 1988); R. G. Petty et al., "Endothelium-The Axis of Vascular Health and Disease," *Journal of the Royal College of Physicians, London* 23: 92–102 (1989); and R. E. Scharf et al., "Thrombosis and Atherosclerosis: Regulatory Role of Interactions Among Blood Components and Endothelium," *Blut* 55: 131–144 (1987). In support of this concept, it has been further shown that patency of both autologous and allogeneic veins used to replace the carotid artery in dogs is dependent upon viability of the vessel and its endothelium. See for example, T. R. Weber et al. "Viable Vein Graft Preservation," *Journal of Surgical Research* 18: 247–255 (1975).

While the principal teachings of the field have emphasized that endothelial cells are critical to graft performance, there are some controversial studies addressing the thrombogenicity of endothelial cell-free vessel surfaces. For example, in M. R. Buchanan et al., "The Basement Membrane Underlying the Vascular Endothelium Is Not Thrombogenic: In Vivo and In Vitro Studies with Rabbit and Human Tissue," *Thrombosis and Haemostasis* 58: 698–704 (1987), it is reported that thrombosis, as measured by platelet adhesion, is not increased by the removal of the endothelial cell layer in rabbit arteries. This observation was hypothesized to result from the secretion of 13-hydroxyoctadecadinoic acid (13-HODE) by endothelial cells onto the basement membrane surface. The validity of these findings was brought into question by J. C. de Graaf et al., in their paper, "Platelet Adhesion to Subendothelial Structures Under Flow Conditions: No Effect of the Lipoxygenase Product 13-HODE," *Thrombosis and Haemostasis* 62: 802–806 (1989). This study reported the opposite conclusion, that 13-HODE is not related to antithrombotic behavior and raised the issue as to whether the lack of platelet reactivity observed by Buchanan et al., supra, was not, in fact, a function of incomplete removal of the endothelial cells. This alternative interpretation is consistent with the findings of J. Aznar-Salatti et al., "Platelet Adhesion to Exposed Endothelial Cells Extracellular Matrixes Is Influenced by the Method of Preparation," *Arteriosclerosis and Thrombosis* 11: 436–442 (1991), in which the extent of endothelial cell removal was shown to be correlated with the degree of platelet reactivity. The greater the degree of endothelial cell removal, the greater the degree of platelet reactivity. Finally, M. Richardson et al., "Wound Healing in the Media of the Normolipemic Rabbit Carotid Artery Injured by Air Drying or by Balloon Catheter Deendothelialization" *American Journal of Pathology* 137: 1453–1465 (1990), showed that air removal of endothelium as used by Buchanan et al., supra, provided only a delay in platelet deposition, not an absence, and that this platelet interaction continued until the vessel surface was again covered by endothelium.

Based on these observations of natural vessel function and platelet reactivity, it has been assumed that the best synthetic blood contact devices capable of thromboresistance similar to the native vasculature would require a blood contact surface of endothelial cells. Consequently, attempts have been made to provide prosthetic surfaces, and specifically vascular grafts, that include or develop an endothelial lining. For example, including U.S. Pat. Nos. 4,883,755, issued to Carabasi et al.; 4,960,423, issued to Smith; 4,804,381 and 4,804,382, issued to Turina et al.; 4,539,716 and 4,546,500, issued to Bell; and 5,037,378, issued to Muller et al., describe means by which living endothelial cell coverage of vascular interfaces can be accomplished to produce antithrombogenicity. These approaches include endothelial cell sodding (Smith), combinations of endothelium with other cells (Bell; Turina et al.), elastin-derived peptides to enhance endothelial cell attachment (Smith), or simple physical means of applying endothelial cells to graft surfaces (Muller et al.).

Although the endothelium is widely recognized as the source of active antithrombogenic behavior of the vessel, it has been shown that the use of nonautologous endothelium in vascular grafts can cause thrombotic failure arising from the immunological recognition of the nonautologous cells. For example, in M. A. Galumbeck et al., "Inhibition of Vessel Allograft Rejection by Endothelial Removal: Morphologic and Ultrastructural Changes," *Annals of Surgery* 206: 757–764 (1987), femoral artery and femoral vein grafts, both with and without endothelium, were transplanted between allogeneic rats. A control group received autologous implants. It was found that the allogeneic vessel implants with the endothelium intact went to failure while those with the endothelium removed remained patent. These results suggest that the antithrombogenicity conferred by the presence of the allogeneic endothelium was outweighed by the recipient immunological reaction to those same cells. The usefulness of nonautologous vessel transplants thus appears to be limited by the theoretical dilemma that arises from this finding, i.e., current understanding of vessel function dictates that the endothelium of the transplanted vessel must be intact to ensure antithrombotic function, but the presence of this same nonautologous endothelium can lead to thrombosis from host immunological response.

In small diameter applications, or grafts used in sensitive areas such as coronary bypass, even limited thrombus generation is a very serious concern. In addition to the questionable patency performance of the above-described grafts in general, none of the above grafts begins to adequately address the patency concerns of small diameter graft applications. It should be noted that enhanced performance of the above-described grafts over existing grafts has not been demonstrated with in vivo implant studies.

In contrast to the above-referenced prior art, it is a primary purpose of the present invention to provide an improved blood contact surface that is less thrombogenic than existing artificial structures, including applications requiring small diameter vascular grafts.

It is another purpose of the present invention to provide an artificial blood contact surface that can be readily manufactured and used.

It is a further purpose of the present invention to identify a previously unrecognized mechanism governing the interaction between blood and natural blood vessel structures and to employ that mechanism to produce a series of improved blood contact structures and methods for making and using them.

These and other objects of the present invention will become evident from review of the following specification.

SUMMARY OF THE INVENTION

The present invention is directed to an improved blood contact surface suitable for use in artificial blood vessels and other implantable appliances, artificial organs, blood transport devices, and similar devices.

Contrary to accepted theories and the teachings of the prior art, if properly separated from endothelial cells, the subendothelial matrix in mammalian blood vessels has been shown to be substantially nonthrombogenic when employed as a primary blood contact surface. This reduced thrombogenicity approximates that of the endothelial cell layer itself. In addition to being a substantially nonthrombogenic surface, the subendothelial matrix is less likely to evoke an immune response in a host, thus making it a substantially improved blood contact surface over virtually all previous attempts to provide artificial or transplanted blood vessels and other blood contact appliances.

The present invention is an improved blood contact surface formed through a series of processing steps that prepares it for use in an apparatus. A general scheme for making the invention is as follows. First, employing natural donor artery, one of a number of endothelial cell stripping techniques is used to produce suitable blood contact surfaces. The resulting blood contact surface is composed of a natural vessel with a preserved subendothelial matrix layer. If desired, additional processing steps can be employed for improved performance, such as treating the vessel to minimize potential calcification of the implant and/or fixation of the vessel, for example. Lastly, the vessel is shielded within a sheath to protect against surrounding tissue ingrowth and to strengthen the vessel as necessary. In addition to being impermeable to cells, the sheath is permeable to molecules, ranging in size from ions to macromolecules.

The use of subendothelial matrix as a direct blood contact surface in the present invention avoids the defects in previous prosthetic blood contact surfaces described above in the background section. First, graft rejection and other immune complications can be reduced or eliminated by using a donor's subendothelial matrix without its endothelial cell layer. Second, in artificial graft production, the use of a preserved natural subendothelial matrix layer in the present invention is less prone to thrombus generation than presently available prosthetic grafts. This allows the present invention to be used in small diameter grafts and other applications that are very sensitive to clotting risks. As a result, the present invention provides a vessel replacement with a greater thromboresistance than other prosthetics.

The improved thromboresistance of the present invention is believed to result from a naturally occurring mechanism present in arteries that resides in the extracellular matrix layer found beneath the endothelium. The improved patency provided by the preserved arteries of the present invention includes the preservation of the subendothelial matrix layer. Accordingly, the present invention is a blood contact surface which comprises a substratum, and a blood contact layer attached to the substratum comprising a preserved subendothelial matrix layer substantially free of donor endothelial cells wherein the subendothelial matrix serves as a primary blood contact surface.

While the present invention is particularly applicable to blood vessels and similar appliances, it may be applied to many areas where substantially nonthrombogenic blood contact surfaces must be provided. Examples of other appliances which may be produced in accordance with the present invention include, without limitation, heart valves, artificial hearts, and artificial organs such as implantable artificial kidneys, among others.

DESCRIPTION OF THE DRAWINGS

The operation of the present invention should become apparent from the following description when considered in conjunction with the accompanying drawings.

DETAILED DESCRIPTION OF THE INVENTION

The present invention is directed to improved blood contact surfaces, such as those used in artificial blood vessels and other blood contact appliances.

Figure 1:
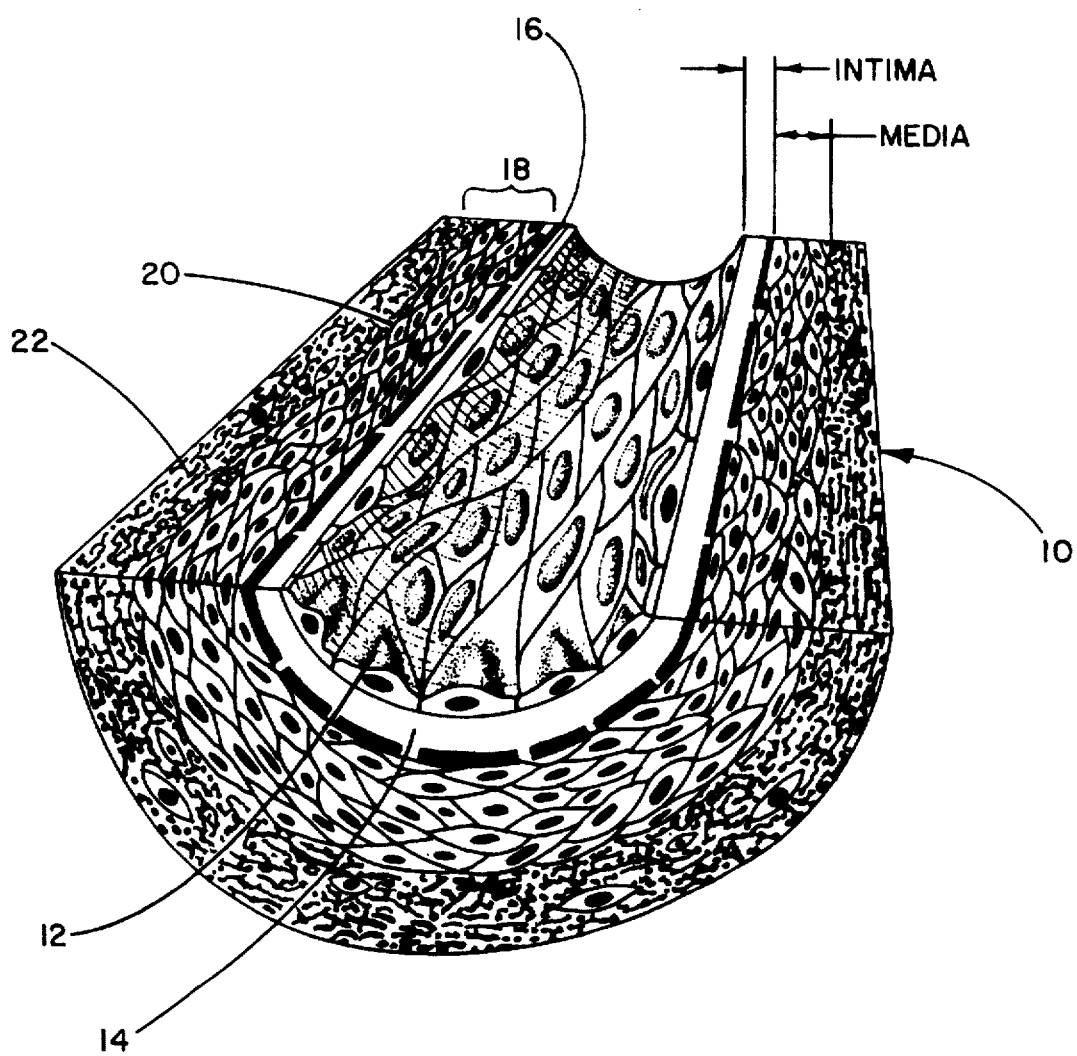
FIG. 1 is a perspective sectional view of a mammalian artery.
Figure 2:
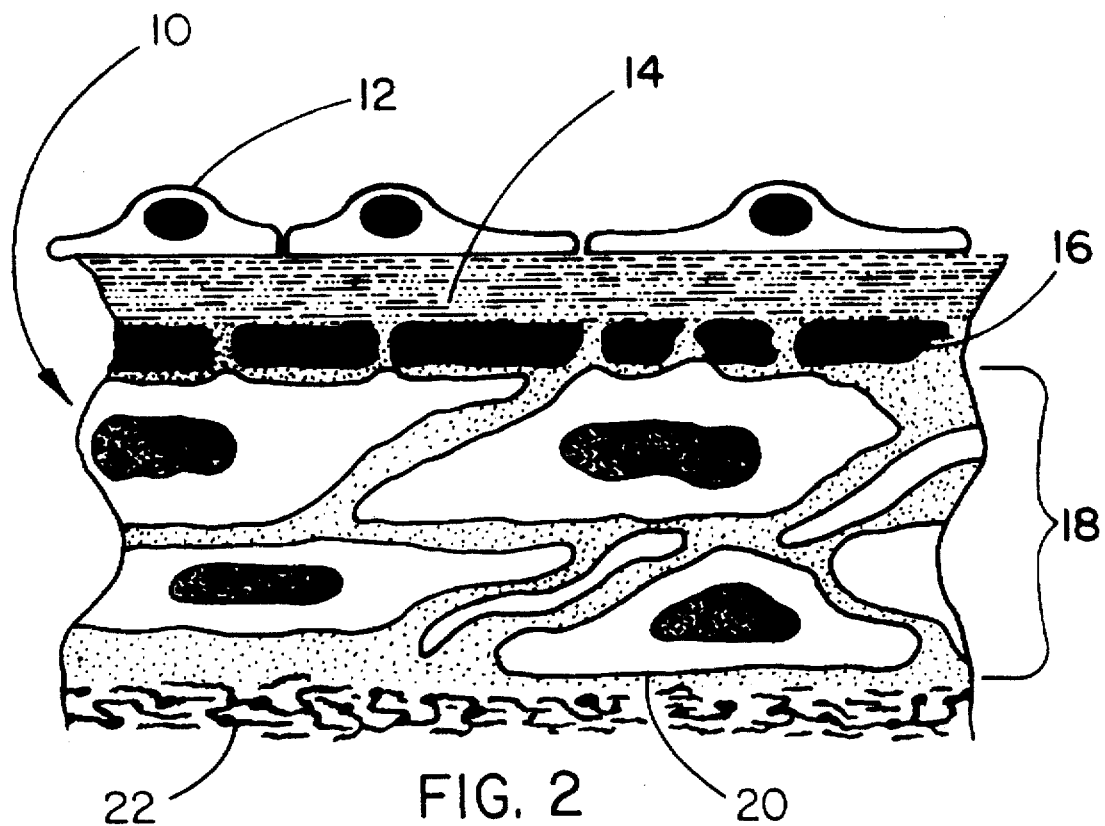
FIG. 2 is a sectional view through the longitudinal axis of a mammalian artery.

By way of introduction, FIGS. 1 and 2 illustrate the structure of a typical mammalian artery (10). The artery (10) structure consists of an intima layer having an innermost layer of endothelial cells (ECs) (12), a subendothelial matrix layer (14) consisting of basement membrane and other extracellular matrix components, and an internal elastic lamina layer (16). External to the intima is a media layer (18) composed of smooth muscle cells (SMCs) (20), and finally a fibrous connective tissue or adventitia layer (22).

As explained in the Background Of The Invention Section above, during normal blood flow, the endothelial cell layer serves as the blood contact surface and, accordingly, must be nonthrombogenic. By contrast, when the blood vessel has been damaged, it is important that thrombosis occurs to prevent blood leakage from the vessel. In this respect, it has been generally accepted that the structures beneath the endothelial cell layer are thrombogenic in order to promote clotting wherever the endothelial layer has been compromised.

Remarkably, it has been discovered that the subendothelial matrix layer (14), immediately beneath the endothelial cell layer (12), is also substantially nonthrombogenic by itself. For example, it has been shown that when a glutaraldehyde-fixed vessel denuded of endothelium is applied in vivo as an arterial substitute, it maintains function not only adequately, but in a manner superior to that of synthetic vessels without a layer of preserved subendothelial matrix. Furthermore, the preserved subendothelial matrix layer of this synthetic vessel provides function superior to that of synthetic vessels with a confluent layer of autologous endothelium. The nonthrombogenic property of the subendothelial matrix layer is demonstrated by the fact that when the subendothelial matrix layer is damaged or removed from the preserved vessel, the performance falls to a level approximately equal to that of a synthetic graft. These results demonstrate that an appropriately processed and preserved subendothelial matrix layer can compensate for the absence of an endothelial lining on a synthetic or naturally derived blood vessel. The term "preserved subendothelial matrix layer," in the instant specification, refers to a subendothelial matrix layer, that has been treated with a fixative solution, such as glutaraldehyde, to chemically stabilize the matrix and thereby preserve the subendothelial matrix layer as a direct blood contact surface.

Accordingly, the present invention uses a preserved subendothelial matrix layer as a direct blood contact surface and thereby resolves many of the above-described deficiencies of the prior art by creating substantially nonthrombogenic blood contact surfaces useful with both synthetic vascular grafts and naturally derived blood vessels. In constructing vascular grafts from biological materials, for example, use of a donor's subendothelial matrix without its endothelial cell layer can reduce or eliminate graft rejection and other immune complications. In artificial graft production, for example, the use of a preserved natural subendothelial matrix layer as the primary blood contact surface of a synthetic vessel is less prone to thrombus generation than presently available prosthetic grafts made of synthetic materials or derived from natural blood vessels. This allows such grafts to be used in situations requiring small diameter grafts, such as peripheral bypasses, coronary bypass applications, or others which are similarly sensitive to clotting risks.

Two general methodologies are used to prepare the blood contact surface of the present invention for use in vascular grafts. One methodology prepares the blood contact surface by using naturally occurring vascular tissue for the graft. The other methodology prepares the blood contact surface by applying a subendothelial matrix layer onto synthetic materials for use as grafts.

Figure 3:
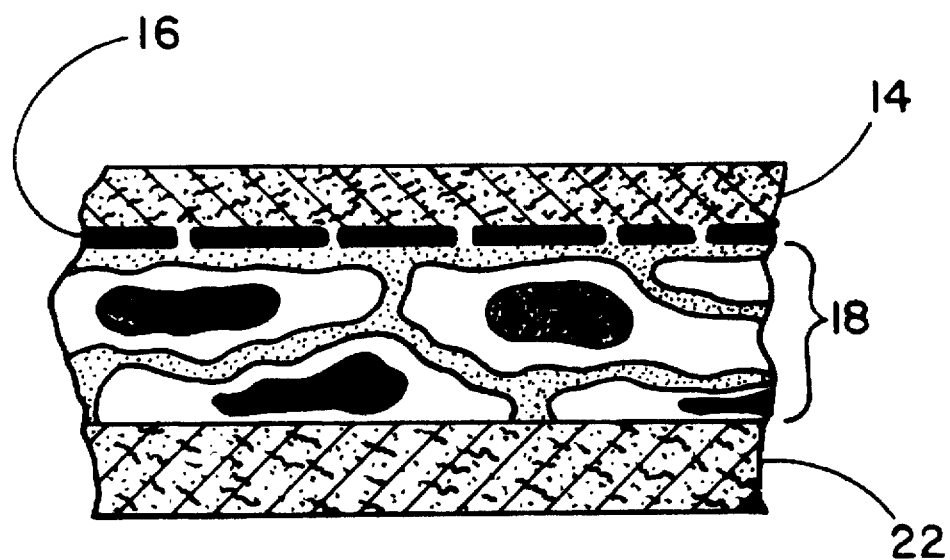
FIG. 3 is a sectional view through the longitudinal axis of one embodiment of the present invention wherein the endothelial cell layer has been removed from the structure of FIG. 2.

When employing natural donor arteries, the present invention uses one of several endothelial cell stripping techniques to produce suitable blood contact surfaces. An optional step may be employed to reduce potential calcification of a donor artery. Next, the subendothelial matrix layer is preserved and the graft is rendered sterile. Following preservation, the resulting blood contact surface as illustrated in FIG. 3 is composed of a natural vessel having a remaining media (18) and adventitia layers (22), an internal elastic lamina layer (16), with a preserved subendothelial matrix layer (14) that serves as a direct blood contact surface.

If desired, the outer diameter of a donor blood vessel can be reduced in order to provide for a thin-walled graft that has better handling characteristics, while retaining the improved patency performance of the present invention. A preferred method for reducing the outer diameter of a donor blood vessel is to digest layers of vascular tissue away from the external surface of the wall of the vessel using proteolytic enzymes. Suitable enzymes for use in this process include, but are not limited to, collagenase, papain, trypsin, chymotrypsin, and elastase, for example. During this process, the interior of the donor blood vessel, including the subendothelial matrix layer, is protected from the action of the proteolytic enzyme.

When employing synthetic materials for a vascular graft, the subendothelial matrix layer may be isolated from donor tissue, applied to the inner surface of a synthetic substratum, and preserved. The resulting preserved subendothelial matrix layer serves as a direct blood contact surface in a vascular graft made of synthetic materials. Each of these processes and embodiments are described in greater detail below.

Preparation and Use of Native Subendothelial Matrix

The starting material for graft fabrication is a donor artery segment obtained from a vertebrate species, preferably a mammalian species including, but not limited to, bovine, porcine, ovine, equine, or primate, including human sources. Avian sources may be useful as well. The blood vessels may be obtained by freezing a limb intact or by immediate dissection of the appropriately sized vessels. If the limb segments are initially frozen, the limbs should be thawed first. Once thawed, the blood vessels are then dissected free from the limbs and placed into a 4° C. saline buffer at physiological pH for processing. Appropriate saline solutions include any number of physiological balanced salt solutions, including, but not limited to, Dulbecco's phosphate-buffered saline, Earle's balanced salt solution, Hanks' Balanced Salt Solution (HBSS), or phosphate buffered saline (PBS), for example.

Processing entails dissection of the extraneous adventitial tissue from the blood vessel and ligation of any branch segments with polymeric suture material. Once these steps have been carried out, the vessel segments are ready for further processing to remove the endothelial cell layer.

The removal of the endothelial cell layer from the subendothelial matrix layer must be carefully performed in order to preserve the nonthrombogenic properties of the subendothelial matrix layer. The use of overly aggressive techniques, such as detergent stripping, were found to damage the subendothelial matrix layer.

There are a number of relatively simple agents and methods that will remove the endothelial cell layer without adversely impacting the subendothelial matrix layer. The subendothelial matrix layer may be treated with a mild chemical stripping solution, such as ammonium hydroxide ($NH_4OH$), for example. One such treatment may involve incubating the vessel lumen in an aqueous $NH_4OH$ solution at a concentration of about 0.01M to about 0.5M, preferably about 0.25M, for a period of about 30 seconds to about 60 minutes followed by flushing the vessel lumen with a buffer solution. In the preferred embodiment, the treatment involves instilling an $NH_4OH$ solution in the lumen of the blood vessel at a concentration of about 0.25M for about 3 to about 5 minutes. A structure resulting from this endothelial cell layer removal is depicted in FIG. 3.

Another suitable technique for endothelial cell removal is the use of air drying of the luminal surface. One contemplated air drying treatment involves flushing the vessel lumen with buffer to remove residual material, followed by air drying for about 5 to about 10 minutes at a flow rate of about 500 to about 2000 cc/min for a 4 mm internal diameter vessel. Preferably, the flow rate is about 1000 cc/min for a 4 mm internal diameter vessel. Following air drying, the vessel lumen is flushed with buffer to remove the endothelial cells and rehydrate the subendothelial matrix layer prior to further processing.

In another embodiment of the present invention, the endothelial cells are removed by exposing the artery to a series of freeze-thaw cycles, preferably greater than two, followed by flushing the artery lumen with a suitable solution such as Hanks' Balanced Salt Solution (HBSS) (1.3 mM $CaCl_2$, 5 mM KCl, 0.3 mM $KH_2PO_4$, 0.5 mM $MgCl_2$, 0.4 mM $MgSO_4$, 138 mM NaCl, 4 mM $NaHCO_3$, 0.3 mM $NaHPO_4$, 5.6 mM glucose).

Once the subendothelial matrix surface has been prepared by endothelial cell removal as described above, a processing step may be employed to prevent or minimize calcification of the vessel tissue once implanted. This technique utilizes a solvent solution to extract predominantly lipid components. One effective treatment involves immersing the artery in a solution of chloroform and methanol ($CHCl_3/CH_3OH$) at, for example, a 2:1 volume:volume ratio, for a period of about 15 to about 60 minutes, with a preferred treatment period of about 20 to about 40 minutes. The artery is then removed from the solvent solution and rehydrated through immersion in a saline solution. Once rehydrated, the graft can then be preserved in a manner described below. The chloroform/methanol treatment does not damage the subendothelial matrix, but serves to limit calcification of the artery once implanted. It is also understood that other anticalcification treatments known to those skilled in the art may be employed as well.

Figure 4:
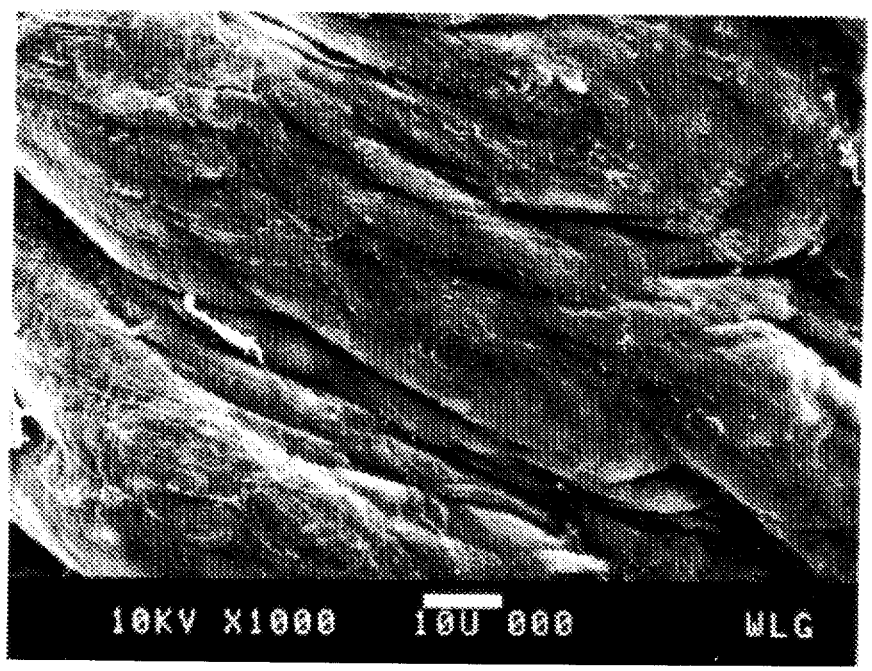
FIG. 4 is a scanning electron micrograph of the preserved subendothelial surface of an artery.

Following rehydration, the artery is pressure fixed in order to preserve the subendothelial matrix layer, to reduce immunogenicity, and to sterilize the vessel segment. This fixation is accomplished by placing the artery within a tube to provide the appropriate diameter for the graft. The lumen of the artery is then filled with a fixing solution, such as, glutaraldehyde, at a concentration of about 0.1–2.5%, in a suitable buffer, at a pressure of about 20.7 kPa to about 34.5 kPa for a period of about 1 to about 72 hours depending upon the concentration of fixative used. Suitable tubes for providing diameter include, but are not limited to, an ePTFE vascular graft such as those available under the trademark GORE-TEX® Vascular Graft from W. L. Gore & Associates, Inc., Flagstaff, Ariz., for example. In addition to glutaraldehyde, suitable fixatives include, but are not limited to, formaldehyde, dialdehyde starches, ethanol, and polyepoxy compounds. Suitable buffers include, but are not limited to, N-2-hydroxyethylpiperazine-N'-2-ethane sulfonic acid (HEPES), acetate, 2(N-morpholino) ethanesulfonic acid (MES), 3-[N-morpholino] propanesulfonic acid (MOPS), tris hydroxymethyl aminomethane, phosphate, and others. In the preferred embodiment, the artery is pressure fixed in greater than about 0.5% glutaraldehyde in 20 mM HEPES buffer for a minimum of about two hours. Other suitable sterilizing agents, such as formaldehyde, may also be used in addition to glutaraldehyde to assure sterility. Following fixation, the arteries are rinsed and stored in a sterile physiological saline solution at about 4° C. until implantation or further use. A representative scanning electron micrograph of the subendothelial matrix layer created is shown in FIG. 4.

As previously described, two of the steps employed in the processing of blood vessels for the current invention are: 1) the removal of the donor endothelium from the surface of the blood vessel; and 2) an extraction of the entire vessel, principally of lipid components, using organic solvents. Remarkably, it has been discovered that these process steps can improve the function of the blood vessel embodiments of this invention in a manner beyond that originally envisioned.

As described above, removal of the donor endothelium exposes the underlying subendothelial matrix and prevents an acute recipient immunologic response to these donor cells. This step is preferably accomplished through the use of a mild chemical stripping solution such as ammonium hydroxide ($NH_4OH$). In the course of developing the embodiments of this invention, however, it has been discovered that the process has an additional effect beyond that of simply removing the original endothelial cells. Blood vessels that have had the endothelium removed by other methods, namely air drying or freeze-thaw cycles, exhibit reduced patency performance in comparison to those that have the cells removed via the $NH_4OH$ treatment. Furthermore, blood vessels that have the endothelium removed via air drying or freeze-thaw exhibit improved performance in patency testing when the vessels are additionally subjected to the $NH_4OH$ extraction.

The organic solvent extraction step is intended to inhibit the mineralization of the tissue-based implants of this invention, particularly those fixed with glutaraldehyde. Similar to the discovery of the base treatment effect described above, vessels that have been subjected to a chloroform and methanol ($CHCl_3/CH_3OH$) extraction provide improved patency performance above vessels that have not been subjected to this process. The unanticipated incremental patency enhancement of this treatment can be recognized as independent of the mineralization process since the contribution is observed in the period prior to implant duration sufficient for mineralization.

The patency contribution of the two above-described processes to the inventive articles of the present invention have been individually assessed. The preferred method of practice, however, is that the two processes both be used to produce the embodiments of this invention. It is believed that each process contributes to the patency function and that the combination is additive, perhaps synergistic.

Figure 5:
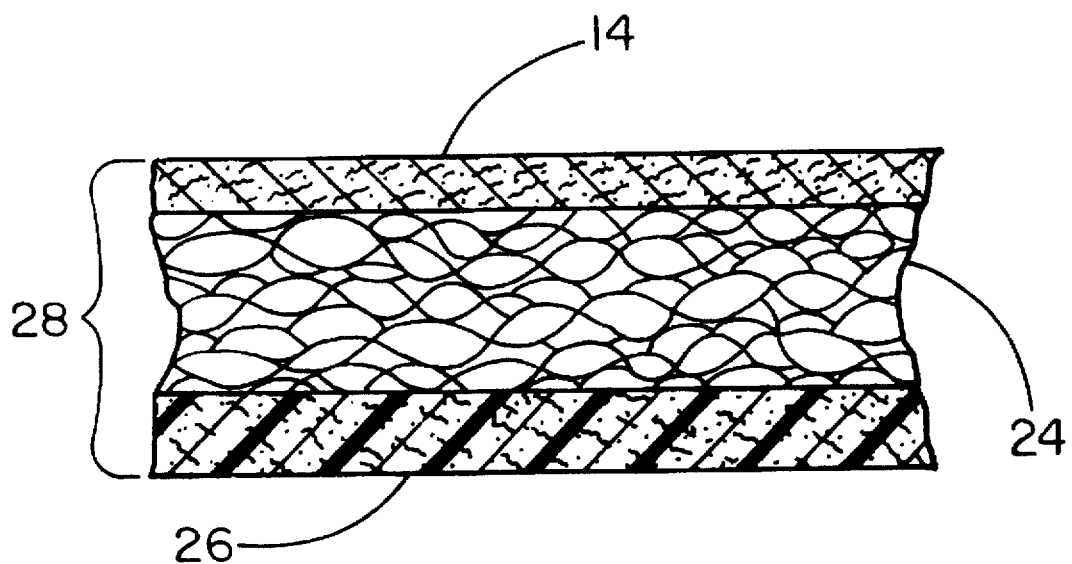
FIG. 5 is a cross-sectional view of another embodiment of an artificial blood vessel of the present invention having the structure of FIG. 3 with a subendothelial matrix encased within a polymeric sheath.
Figure 6:
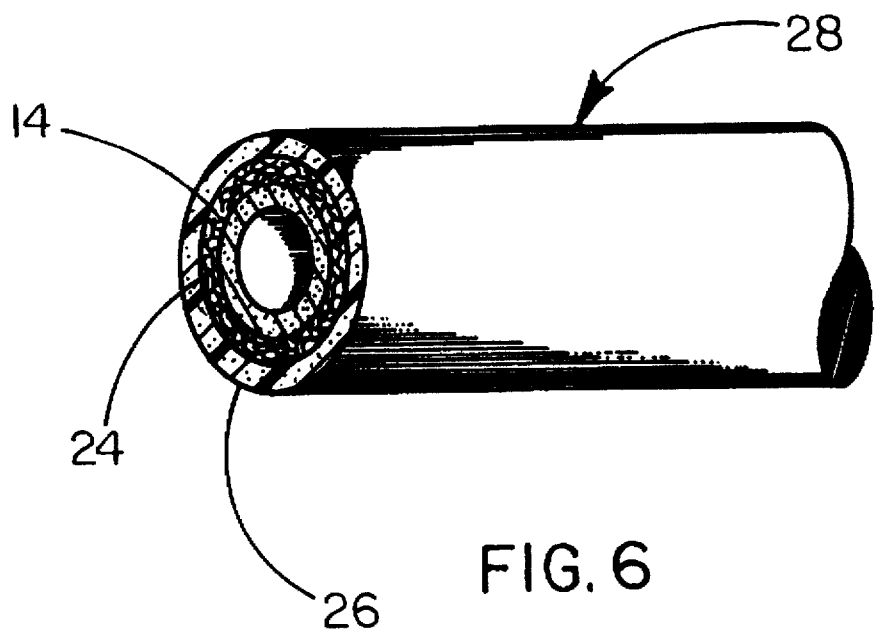
FIG. 6 is another view of the embodiment of the present invention illustrated in FIG. 5.

In the present invention, it is preferred to surround the processed donor artery in a sheath (26) made of synthetic material to form a composite (28) as depicted in FIGS. 5 and 6. Suitable materials for the sheath include, but are not limited to, polytetrafluoroethylene (PTFE), polyethylene terephthalate, polypropylene, fluorinated ethylene propylene (FEP), and combinations of the above, among others. It is a primary function of the sheath to assist in maintaining the nonthrombotic properties of a processed donor artery. This is accomplished by excluding host cells from the donor artery while permitting bulk flow of biological substances across the thickness of the sheath to and from the processed artery. The ideal sheath material is permeable to macromolecules, while being impermeable to cells. The term "imacromolecules" is understood to include, but not be limited to molecules having a molecular weight up to and including about 2,000,000 MW, for example. Preferred materials for the sheath are materials that are microporous, with microporous ePTFE being most preferred.

The pore size that is effective in blocking cell passage across the thickness of the sheath is dependent upon the thickness of the wall itself and the tortuosity of the pore connecting the outer surface with the inner surface of the sheath. In the case of regular uniform pores in a thin sheath construction (about 10–20 μm in thickness) the pores must be selected to be less than about 3.0 μm in diameter. This value is based upon Boyden chamber assays where the limit of fibroblast migration through straight, uniform pores is about 5–8 μm and the limit of leukocyte invasion through straight, uniform pores is about 3–5 μm. (A. Albini et al., "Fibroblast Chemotaxis," *Collagen Related Research*, 5: 283–296, (1985); W. Morzycki et al., "Tumour Necrosis Factor-alpha but not Interleukin-1 Induces Polymorphonuclear Leucocyte Migration through Fibroblast Layers by a Fibroblast-Dependent Mechanism," *Immunology*, 74: 107–113, (1991)) In the case of a thicker, more tortuous, or laminate structure, the individual pores can be somewhat larger and still serve as an effective barrier to the passage of cells across the layer.

For an ePTFE or similar fibrillated sheath, the pore size of the sheath is directly related to the fibril length of the sheath material. The fibril length should be chosen to form pores that resist cellular access through the sheath, while remaining permeable to macromolecules. In defining the resistance to cell ingrowth, a noncellular assay method has been developed. Based upon the published values that 3.0 μm represent the lower limit of cell permeability through straight pores, 3.0 μm microspheres can be used to mechanically determine whether a given sheath will exclude particles of this diameter. Consequently, any sheath material that excludes 3 μm microspheres should effectively prevent cellular movement across the sheath.

In the present invention, the sheath properties can be selected to supply mechanical properties to the processed donor artery in addition to having the aforementioned permeability and cell exclusion properties. One skilled in the art will recognize that minimum mechanical integrity requirements exist for each blood appliance application. One minimum requirement is that the appliance resist the forces imposed by blood pressure for the intended duration of a given application. Therefore, the configuration must resist the hoop stress induced by blood pressure without rupture or aneurysm formation, and must similarly resist the stresses induced at the anastomosis without rupture, excessive suture hole elongation, or false aneurysm formation. In addition to these minimal mechanical requirements, it is preferred that the sheath be of sufficient strength to serve mechanically as a blood vessel substitute even in the absence of the vascular tissue it is intended to surround. In this embodiment, a synthetic sheath is placed around the donor vascular tissue, and the support is thus a composite of that provided by the donor tissue and the synthetic sheath. FIGS. 5 and 6 illustrate this composite structure having a subendothelial matrix layer (14), remaining media and adventitia layers (24), a sheath (26) surrounding these layers, together forming a composite (28). While the biological tissue is subject to degradative processes that could reduce its strength below that required for the application, the synthetic can resist these same processes where the appropriate polymer and fabrication are chosen.

One method of constructing the sheath is by wrapping a mandrel with multiple layers of ePTFE film, such as those described in U.S. Pat. No. 3,953,566 and 4,187,390, both issued to Gore, each of which is incorporated herein by reference, and adhering the film to itself by heating the film and mandrel at about 380° C. for about 10 to about 20 minutes. The film tube is removed from the mandrel and prepared tissue graft installed in the lumen of the polymeric tube. Other materials, or combinations of materials, may be applied to the tissue tube similarly, using temperatures and times appropriate for the physical properties of the chosen material.

Other methods of manufacturing the sheath material include placing a processed artery onto a mandrel and wrapping the artery with multiple layers of an ePTFE and FEP composite film, and heating the film layer very briefly from to a temperature above the melting point of the FEP film, i.e. about 271° C., to adhere the film wrap to itself on the outer surface of the vessel. The FEP-coated ePTFE film is made by a process which includes the steps of:

a) contacting a porous PTFE substrate, usually in the form of a membrane or film, with another layer which is preferably a film of FEP or alternatively of another thermoplastic polymer;

b) heating the composition obtained in step (a) to a temperature above the melting point of the thermoplastic polymer;

c) stretching the heated composition of step (b) while maintaining the temperature above the melting point of the thermoplastic polymer; and d) cooling the product of step (c).

Another sheath construction method is the fabrication of a tubular form of ePTFE constructed according to U.S. Pat. No. 3,593,566 to Gore, which is incorporated herein by reference, using a uniaxial expansion. The processed blood vessel is inserted into the ePTFE tube so constructed. As in the other forms of the sheath, the tubular form must be permeable to the passage of macromolecules but exclude the passage of cells.

Construction of the sheath is described in a U.S. Patent application of Bruchman et al., entitled "Cell Excluding Sheath For Vascular Grafts," U.S. Ser. No. 08/235,045, filed Apr. 29, 1994, which is incorporated herein by reference.

The permeability characteristics of the sheath can be evaluated by removing the sheath from the processed artery and subsequently testing with markers of known size, such as dextrans and polystyrene microspheres. For example, dextran, labelled with fluorescein (Sigma Chemical Co., St. Louis, Mo.), with an average molecular weight of about 2,000,000 MW can be used to test the ability of the sheath to pass macromolecules. Cell permeability of the sheath can be tested with polystyrene microspheres (Polysciences, Inc., Warrington, Pa.), with a diameter of about 3.0 μm, having a concentration of about 2.5% solids in suspension, for example.

When testing the sheath for permeability with colored markers, the markers are suspended as an aqueous solution or suspension at concentrations sufficient to provide a distinctly visible color. Preferred concentrations of the compound of the marker solution is approximately 0.2 mg dextran/ml solution and approximately 0.02 ml microspheres/ml suspension, to yield about $4.5 \times 10^7$ beads/ml suspension. The evaluation of the permeability of the sheath occurs at about 23° C. The sheath is prepared for permeability testing by rendering it permeable to water, if necessary. For example, sheaths constructed of ePTFE are wetted with 100% ethyl alcohol and then flushed with water to remove the alcohol before testing.

To test the permeability of the sheath to macromolecules, the dextran test solution is instilled in the lumen of a sheath and pressurized to about 20.7 kPa using a syringe. The contents of the syringe are forced through the sheath and the liquid that filters through the sheath wall is collected and visually inspected against a white background for evidence of the colored dextran.

In preparation for testing the permeability of a sheath for cells, the number of microspheres in the suspension are determined by using an appropriate counting device, such as a hemacytometer, for example. The permeability of the sheath for cells is then tested by forcing the microsphere-containing suspension through the sheath material at about 20.7 kPa using a syringe. The syringe is refilled with water and the water also forced through the sheath at about 20.7 kPa. The liquid that filters through the sheath wall is collected and subjected to centrifugation at about 300×g for about 10 minutes. The supernatant is decanted and discarded and the pellet of microspheres is resuspended in a known volume of water. The number of microspheres in the resuspended pellet are counted and compared with the original suspension. The number of microspheres that pass through the sheath are expressed as a percentage of the number introduced into the lumen of the sheath.

An appropriate sheath for this application will pass the 2,000,000 MW dextran at pressures at or below about 20.7 kPa so that the solution that filters through the sheath is visibly colored when viewed against a white background. Additionally, the sheath will not allow more than about 5% of the 3.0 μm microspheres to pass at about 20.7 kPa.

As previously described, a key element of the current invention is the use of a preserved subendothelial matrix layer as a blood contact surface. The invention is practiced preferably by leaving the preserved subendothelial matrix layer in situ, and grafting the tissue with this layer intact. An alternative embodiment is the removal of the subendothelial matrix layer from the surface of the donor cardiovascular tissue prior to preservation and reapplying the subendothelial matrix layer to a synthetic surface. The anticalcification and preservation steps described above are then performed on the subendothelial matrix layer on the synthetic surface. In this case, the synthetic component supplies all of the required mechanical support for the prosthesis.

The first step in the process of applying subendothelial matrix layer to a synthetic substratum layer is the removal of the endothelium from the donor tissue. The subendothelial matrix layer is then mechanically removed from the donor tissue using, for example, a scalpel blade. Only that layer of extracellular matrix superficial to the internal elastic lamina is removed. The intact internal elastic lamina is left attached to the donor tissue.

A number of methods of attachment of the subendothelial matrix layer to a synthetic substratum layer are possible. One preferred method of attachment of the subendothelial matrix layer to the synthetic substratum is to mechanically entrap the derived subendothelial matrix layer onto the synthetic substratum. This is accomplished, for example, by suspending the subendothelial matrix layer derived from the luminal surface of bovine aorta in HBSS. An ePTFE vascular graft is wetted in 100% ethanol after mounting on syringe fittings and the solution containing the subendothelial matrix suspension forced through the interstices of the microporous graft using syringe pressure. As the solution is forced through the graft, the fragments of the subendothelial matrix are left behind entrapped in the interstices and on the surface of the graft.

The subendothelial matrix layer prepared by any of the above processes contains numerous extracellular matrix components. Using immunocytochemical assays, it has been determined that this subendothelial matrix layer includes chondroitin sulfate proteoglycans, fibronectin, collagen Type I, collagen Type IV, collagen Type III, elastin, and glycosaminoglycan-bearing proteoglycans, for example.

Structures of Vessels Made in Accordance with the Present Invention

Without intending to limit the scope of the present invention, the following examples illustrate how the present invention can be made and used. The experimental results of the following examples are summarized in Table 1 at the end of the examples section.

EXAMPLES

Example 1

This example demonstrates that an artery-derived vascular graft having a preserved subendothelial matrix layer of the present invention has improved patency compared to a control artery-derived vascular graft lacking a subendothelial matrix layer.

Pairs of carotid artery segments were removed from donor greyhound dogs, placed into vials containing 15% dimethyl sulfoxide/Hanks' Balanced Salt Solution (DMSO/HBSS), and stored frozen under liquid nitrogen until subsequent processing. At processing, each vial was immersed in a water bath at 37° C. until thawed. Each pair of arteries was removed from the vial, rinsed in normal saline, and the adventitia removed by manual dissection. One artery of each pair was selected for stripping of the subendothelial matrix layer and served as the control graft. The other artery of the pair was processed to preserve the subendothelial matrix layer intact and served as the inventive graft.

The subendothelial stripping procedure was performed by grasping one end of the control artery segment with hemostats and forcibly drawing a cylindrical length of extruded polytetrafluoroethylene (PTFE) with a sharp end against the lumen down the length of the vessel. This procedure was repeated several times to ensure the disruption and removal of the subendothelial matrix layer. The inventive vessel segment having a preserved subendothelial matrix layer had the luminal surface exposed to flowing air (about 1000 cc/min) for 5 minutes to ensure no remaining donor endothelium. Scanning electron microscopy (SEM) inspection of representative samples of artery subjected to flowing air confirmed near total loss of the native endothelium and the maintenance of the subendothelial matrix layer. It is understood that for purposes of the present invention, removal of native endothelium from the subendothelial matrix layer in amounts greater than about 80% is considered to render the subendothelial matrix layer substantially free of donor endothelial cells. Both control and inventive vessel pairs were then mounted on barbed fittings using 3-0 silk suture and placed inside a thin walled 3.0 mm GORE-TEX® Vascular Graft (W. L. Gore & Associates, Inc., Flagstaff, Ariz.) sleeve to provide a finished internal diameter of about 2.5 mm. The vessel pairs were rinsed with saline, immersed in 2.5% glutaraldehyde in 0.2M Sorenson's phosphate buffer (pH 7.0–7.2), and the solution forced into the lumen at 27.6 kPa pressure for 2 hours. Using sterile technique, the ePTFE sleeves were then removed, the ends of the artery segments were trimmed, the vessels rinsed thoroughly in sterile normal saline, and stored in sterile normal saline at 4° C. until implantation.

These control and inventive grafts were implanted as test pairs into the brachial arteries of 6 adult greyhounds dogs. One graft of each pair was implanted into one brachial artery of the dog so that a direct comparison of the vessels within each dog was achieved. The vessel grafts, 2.5 cm long with an internal diameter of 2.5 mm, were a good diameter match to the native brachial artery of the adult greyhound recipients. Standard end-to-end surgical technique was used for implantation and no anticoagulants or antiplatelet agents were administered to the dogs at any time. The course of the implants was followed using contrast angiography and duplex ultrasound examination. At two weeks postoperatively, each pair of brachial implants was surgically exposed and the patency tested by transecting the artery distal to the implant location. The inventive graft with the preserved subendothelial matrix layer were confirmed to be patent in six of six (6/6) cases, while the control grafts with a disrupted subendothelial matrix layer were patent in only one of six (1/6) cases. In conclusion, the inventive graft demonstrates that a preserved subendothelial matrix layer provides improved patency compared to control grafts lacking a subendothelial matrix layer.

Example 2

This example demonstrates that treatment of the subendothelial matrix layer of the present invention with a solution of chloroform and methanol reduces calcification of the graft following implantation, without affecting the preservation of the subendothelial matrix layer of the graft.

Distal leg arteries from cows were obtained at slaughter and stored frozen at –20° C. until processing. After thawing, distal arteries having an internal diameter of about 2–3 mm were identified and dissected free of the animal. The adventitia was removed by dissection, the branches were tied, and the vessel segments were mounted on barbed fittings. To ensure the absence of donor endothelium, the lumen of each vessel segment was air dried with flowing air for about 5 minutes, followed by a brief rinsing in HBSS. Each vessel segment was cut in half. One-half of the segment was arbitrarily designated as the inventive graft and one-half as the control graft. The inventive graft was then immersed in a solution of chloroform and methanol ($CHCl_3/CH_3OH$; 2:1 V:V) for about 30 minutes at room temperature. The inventive graft was then rehydrated in normal saline for about 30 minutes, sleeved in a commercially available 3.0 mm thin walled GORE-TEX® Vascular Graft (W. L. Gore & Associates, Inc., Flagstaff, Ariz.) to provide a finished internal diameter of about 2.5 mm, and perfused with a solution of 2.5% glutaraldehyde in 0.2M Sorenson's phosphate buffer (pH 7.0) for 2 hours at 27.6 kPa. After fixing, the sleeve was removed, the ends of the vessel segment trimmed, and the segment rinsed in two 500 ml changes of sterile saline for a total of 30 minutes to remove residual glutaraldehyde. The treated artery segment was stored in sterile normal saline at 4° C. until implantation. The control artery segment was similarly processed except that it was not subjected to the $CHCl_3/CH_3OH$ extraction.

The inventive and control grafts were implanted as a test pair into the brachial arteries of an adult greyhound dog with one brachial artery receiving the inventive extracted bovine test graft and the contralateral artery receiving the non-extracted control graft. The grafts, 2.5 cm in length, were implanted using standard end-to-end surgical technique. No anticoagulants or antiplatelet agents were administered at any time. Each dog was followed daily for the first two weeks using a doppler ultrasound duplex scanner, and weekly thereafter. Contrast angiography was also periodically employed to confirm patency status. The grafts were exposed at 393 days postoperatively and the patency tested by transecting the artery distal to the graft location. Both grafts were found to be patent. The control non-extracted bovine graft was found to be heavily mineralized with longitudinal cracking on the lumen after opening. The inventive extracted bovine test graft had no grossly or microscopically observable calcium deposition. Thus, chloroform and methanol treatment reduced calcification of the graft wall while not affecting the preservation of the subendothelial matrix layer.

Example 3

This example demonstrates that a donor artery with a preserved subendothelial matrix layer of the present invention, treated with a solution of chloroform and methanol to prevent or reduce calcification of the graft provides improved patency compared to control ePTFE grafts.

Distal leg arteries, 2–3 mm in diameter, were obtained from cows and processed like the chloroform and methanol extracted inventive graft detailed in Example 2. These grafts were implanted into greyhound brachial arteries as test pairs using a 2.5 mm internal diameter 30 μm GORE-TEX® expanded PTFE tube (W. L. Gore & Associates, Inc., Flagstaff, Ariz.) as the control graft.

The 2.5 mm internal diameter ePTFE tubing used for controls in this example was constructed from CD 123 fine powder PTFE resin (ICI Americas) as taught in U.S. Pat. No. 3,953,566 to Gore, which is incorporated herein by reference. The tubes were expanded by stretching to produce a mean fibril length of about 30 μm. The finished tubes had an internal diameter of about 2.5 mm and a wall thickness of about 0.33 mm.

The fibril length of the porous expanded PTFE tubes produced as above is defined herein as the average of ten measurements between nodes connected by fibrils in the direction of expansion. Ten measurements are made in the following manner. First, a photomicrograph is made of a representative portion of the sample surface, of adequate magnification to show at least five sequential fibrils within the length of the photograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

One brachial artery received the extracted bovine inventive graft and the contralateral artery received the 30 μm ePTFE control graft. The grafts, 2.5 cm in length, were implanted using standard end-to-end surgical technique. No anticoagulants or antiplatelet agents were administered at any time. Each dog was followed daily using a doppler ultrasound duplex scanner for the first two weeks postoperatively and weekly thereafter. Contrast angiography was also employed to determine patency status in the event of ambiguous ultrasound results. At one month, it was found that the extracted bovine inventive grafts were patent in three of five (3/5) cases and the synthetic ePTFE control grafts were patent in one of five (1/5) cases. In conclusion, preservation of the subendothelial matrix layer and reduction of calcification by chloroform and methanol treatment provides improved patency compared to control ePTFE grafts.

Example 4

This example demonstrates that a donor graft with a preserved subendothelial matrix layer of the present invention provides improved patency compared to a commercially available graft with a preserved endothelium.

Distal leg arteries, 4–5 mm diameter, were obtained from cows and processed as described in Example 2 for the chloroform and methanol extracted inventive graft, except that they were pressure fixed with glutaraldehyde inside a 6 mm sleeve tube to provide a finished internal diameter of about 5.0 mm. The result of this processing is a graft without endothelial cells but having an intact, preserved subendothelial matrix layer. These inventive grafts were compared in implant studies to a commercially available 5.0 mm graft of bovine source, manufactured by Biocor Industria E Pesquisas LTDA, Brazil, that served as the control graft. The Biocor graft was also glutaraldehyde fixed but SEM inspection revealed a uniform donor endothelium present on the graft luminal surface. Prior to use, both varieties of graft were rinsed in multiple changes of sterile saline, and stored refrigerated in sterile normal saline until implantation.

Using standard end-to-end surgical technique, 4.0 cm lengths of both grafts were implanted as test pairs into the femoral arteries of 6 adult greyhound dogs. One femoral artery of each dog was implanted with the Biocor bovine graft and the contralateral artery received an inventive graft processed as described above. No anticoagulants or antiplatelet agents were administered at any time. Each dog was followed daily for the first two weeks using a doppler ultrasound duplex scanner, and weekly thereafter. Contrast angiography was also employed to determine patency status in the event of ambiguous ultrasound results. At one month, the extracted bovine inventive grafts having an intact subendothelial matrix layer without endothelial cells were patent in three of six (3/6) cases while the control Biocor bovine grafts having an intact endothelium were patent in zero of six (0/6) cases. In conclusion, the preserved subendothelial matrix layer of the inventive graft provides improved patency compared to a commercially available biological graft having a preserved endothelial cell layer.

Example 5

This example demonstrates that a donor graft having a preserved subendothelial matrix layer of the present invention provides improved patency performance compared to a donor graft having had the endothelial cell layer removed with a routine detergent treatment.

A pair of arteries was removed from a donor dog, placed in 15% DMSO/HBSS, and stored in liquid nitrogen. For processing, the graft pair was thawed, rinsed in HBSS, and the adventitia was removed by dissection. One vessel of the pair was processed as disclosed in the present invention to provide a donor graft with a preserved subendothelial matrix layer. The other vessel was processed in accordance with the teachings of U.S. Pat. No. 4,776,853, issued to Klement et al., which is incorporated herein by reference, and outlined below, to provide a donor graft with the endothelial cell layer removed from the graft.

The inventive graft of the present invention was prepared by placing the artery segment into 0.25M $NH_4OH$ for one minute to ensure the absence of donor endothelium, followed by rinsing in HBSS. In a subsequent step, the artery segment was soaked in a solution of $CHCl_3/CH_3OH$ (2:1 V:V) for about 30 minutes to inhibit calcification following implantation. During the process, the lumen was periodically flushed with fresh solution. The graft segment was rehydrated in HBSS, sleeved with a 3.0 mm thin walled GORE-TEX® Vascular Graft (W. L. Gore & Associates, Inc., Flagstaff, Ariz.) to maintain the lumen at about 2.5 mm during the subsequent pressure fixation step, and attached to barbed fittings. The graft vessel was then pressure fixed using 0.25% (V:V) glutaraldehyde in 0.2M Sorenson's phosphate buffer (pH 7.0–7.2) at 27.6 kPa pressure for 2 hours. After pressure fixation, the artery graft segment was withdrawn from the sleeve and fixed in 0.25% glutaraldehyde solution an additional 8–24 hours. In a final step, the artery graft segment was removed from the glutaraldehyde solution, rinsed several times in normal saline, and stored in sterile normal saline at 4° C. until use.

The control graft was prepared by using the other segment of the thawed donor artery pair and subjected to the process described in Example 1 of U.S. Pat. No. 4,776,853, issued to Klement et al. Specifically, the artery segment was first incubated in 10 mM TRIS buffer at 4° C. for 24 hours (100:1 volume of solution:vessel) followed by incubation in 1% Triton X-100 detergent at 4° C. for about 24 hours (same volume ratio). Subsequently, the segment was washed 3 times in 100:1 volumes of purified sterile water and incubated 45 min in HBSS/10 mM HEPES and 50 U/ml penicillin/streptomycin (Gibco) at 37° C. while rocking. In a further processing step, the segment was subjected to RNase A and DNase I (both acquired from Sigma Chemical Company, St. Louis, Mo.) enzymatic digestion for 4.5 hours while rocking and again washed in purified water. The segment was then incubated in 1% solution of sodium dodecyl sulfate (SDS) for 24 hours at room temperature followed by washing in 3 changes of 100:1 volumes of purified sterile water over 24 hours. The vessel was stored in HBSS/10 mM HEPES with 100 U/ml penicillin/streptomycin at 4° C. until use. The processing of this control graft substantially removes all of the endothelial cells.

One vessel of each description was implanted into the brachial artery of an adult greyhound dog, with one brachial artery receiving the inventive graft processed as described above and the contralateral brachial artery receiving the above described control graft. The grafts, 2.5 cm in length and 2.5 mm diameter, were implanted using standard end-to-end surgical technique. No anticoagulants or antiplatelet agents were administered at any time. The dog was followed daily using a doppler ultrasound duplex scanner for the first two weeks postoperatively and weekly thereafter. It was found that the control graft had occluded by the fourth day postoperative, while the inventive graft of the present invention remained patent. This was further documented with contrast angiography at 14 days postoperative. The grafts were removed at one month post-implant and the patency status of the graft documented by cutting the host artery distal to the graft location and checking for blood flow. It was found that the inventive graft remained widely patent at one month and was largely free of thrombus deposition. The control graft, as earlier documented, was found to be occluded and the anastomoses filled with organized tissue, suggesting an occlusion of long duration. Thus, the above-described detergent treatment of the control biological graft to remove the endothelial cell layer had a negative effect on patency compared to the improved patency performance observed with the inventive graft having a preserved subendothelial matrix layer.

Example 6

Further to Example 5, above, this example illustrates an additional experiment in which the patency performance of a donor graft treated with de-endothelializing detergent is compared to the patency performance of a donor graft having the preserved subendothelial matrix layer of the present invention. In the experiment, allogeneic arteries were implanted into the femoral arteries of four adult greyhound dogs. The artery pairs intended for grafting were carotid arteries obtained from donor dogs. One artery of each pair was selected as the inventive graft and processed as detailed for the inventive graft in Example 5 above, except that the grafts were 4.0 mm internal diameter and 4.0 cm in length. The other artery was selected as the control graft and processed as the control graft described in Example 5 above. These graft pairs were implanted into the femoral arteries of each dog, one per side, so that each dog had a direct comparison of the two graft types. At one month, the grafts were surgically exposed and tested for patency by transecting the artery distal to the graft location. It was found that four of four (4/4) of the inventive grafts had remained patent while two of four (2/4) of the control grafts were patent. It was further found that the control grafts had lost mechanical integrity in two of four (2/4) cases when the grafts tore during removal. It was found that the graft walls were much weaker than at the time of implantation. Thus, the detergent treatment of biological grafts had a negative effect on patency compared to the improved patency observed with the inventive graft.

Example 7

The non-ionic detergent Triton X-100 has been employed as a processing step in the treatment of arteries in a number of patents and publications. See, for example, U.S. Pat. Nos. 4,801,299, issued to Brendel et al., and 4,776,853, issued to Klement et al. Its effectiveness in the present invention was tested as follows.

Distal leg arteries were obtained from cows as described in Example 2, above. The size was chosen to provide an internal diameter of about 2–3 mm. After dissection, the luminal surface of the vessels were air dried to ensure the removal of the donor endothelium. The arteries were pooled and then randomly assigned to the test vessel group or to the control vessel group. The test vessel was extracted in 1% Triton X-100 for 42 hours. The control vessel was not extracted with the Triton X-100 detergent. Both vessels were then rinsed for 2 hours in each of the following solutions: saline, 12% ethanol, and again in saline. Both vessels were mounted on barbed fittings, sleeved with a 3 mm ePTFE tube to provide a finished internal diameter of 2.5 mm, and pressure perfused with a solution of 2.5% glutaraldehyde in 0.2M Sorenson's phosphate buffer (pH 7.0) for 2 hours at 27.6 kPa pressure. After fixation, the vessels were rinsed in two changes of sterile saline and stored at 4° C. in sterile normal saline until required for implantation. The control graft was processed like the inventive graft but without the Triton X-100 endothelial cell-extraction step.

Using standard end-to-end surgical technique, 2.5 cm lengths of both graft types were implanted as test pairs into the brachial arteries of 7 adult greyhound dogs. One brachial artery of each dog received the Triton X-100 test graft and the contralateral artery received the non-extracted control graft. No anticoagulants or antiplatelet agents were administered at any time. Each dog was followed daily using a doppler ultrasound duplex scanner for the first two weeks and weekly thereafter. Contrast angiography was also employed to determine patency status in the event of questionable ultrasound results. At 3 weeks postoperative, zero of seven (0/7) of the detergent-extracted test grafts were patent, while the non-extracted control grafts were patent in five of seven (5/7) cases. Thus, Triton X-100 extraction of biological grafts produced a negative effect on the patency performance of the present invention.

Example 8

Sodium dodecyl sulfate (SDS) is an anionic detergent that denatures proteins by disrupting noncovalent interactions. The use of SDS is specified in a number of tissue preparations intended for implant, such as, for example, U.S. Pat. Nos. 4,801,299 issued to Brendel et al.; 4,776,853 issued to Klement et al.; 4,323,358 issued to Lentz et al.; and 4,553,974 issued to Dewanjee. The effect of SDS on the patency performance of the present invention is demonstrated in this example.

Pairs of carotid artery segments were obtained from greyhound dogs and endothelial cells removed as in Example 1. The artery segments were then stored frozen in 15% DMSO/HBSS. After thawing the adventitia was removed, and one artery of each pair selected for testing with SDS extraction. The other artery from each pair served as the control artery. The test segments were mounted on barbed fittings, filled with 4% (W:V) SDS in water, and pressurized to 27.6 kPa while immersed in the same solution. The test segments were extracted for 20 hours while immersed in approximately 100 ml of the SDS solution. The solution in the lumen of the test segment was replaced every hour for the first three hours of the extraction. After extraction, the test segments were rinsed thoroughly in distilled water to remove residual SDS. Both the test and control artery segments were then sleeved with 3.0 mm ePTFE tubes to provide a finished internal diameter of about 2.5 mm and barbed fittings were reattached. Both artery segments were then perfused with 2.5% glutaraldehyde in Sorenson's phosphate buffer (pH 7.0) for 2 hours at 27.6 kPa pressure. After fixation, both segments were rinsed in two changes of sterile normal saline, and stored at 4° C. in sterile normal saline until required for implantation. Accordingly, the non-extracted control graft was prepared like the test graft except for the SDS extraction step.

The patency performance of the test and the control arteries were compared in implant studies. Using standard end-to-end surgical technique, 2.5 cm lengths of both grafts were implanted as test pairs into the brachial arteries of 5 adult greyhound dogs. One brachial artery of each dog received the SDS-extracted test graft and the contralateral artery received the non-extracted control graft processed without the SDS extraction. No anticoagulants or antiplatelet agents were administered at any time. Each dog was followed daily using a doppler ultrasound duplex scanner for the first two weeks and weekly thereafter. Periodic contrast angiography was also employed to confirm patency status. In four of five (4/5) cases, the SDS-extracted test graft occluded on the first post operative day. At three months, four of five (4/5) of the non-extracted control grafts were patent while only one of five (1/5) of the SDS-extracted test grafts was patent. At six months, three of five (3/5) non-extracted control grafts were patent while zero of five (0/5) of the SDS-extracted test grafts were. In conclusion, SDS extraction of the test graft had a negative effect on the patency performance of grafts prepared according to the present invention.

Example 9

The proteolytic enzyme ficin has been used to digest potentially immunogenic portions of donor tissues. The use of this enzyme to treat tissues, specifically blood vessels intended for implantation, has been practiced on a commercial basis and is specified in the following U.S. Pat. Nos. 2,900,644 issued to Rosenberg; 3,927,422 issued to Sawyer; 4,383,832 issued to Fraefel et al.; 4,098,571 issued to Miyata; and 4,083,066 issued to Schmitz. The effect of ficin digestion on donor arterial tissue prepared in accordance with the present invention is demonstrated in this example.

Pairs of carotid artery segments were removed from donor greyhound dogs, placed into vials containing 15% DMSO/

HBSS, and stored frozen under liquid nitrogen until subsequent processing. At processing, each vial was thawed in a 37° C. water bath, rinsed in normal saline, and the adventitia was removed by dissection. One artery of each pair was assigned to the test group and the other artery assigned to the control group.

The ficin treated test artery segment was processed by incubation in a 1% solution of ficin in a phosphate-citrate buffer (pH 7.4) for 3 hours at 37° C. The artery segment was then placed into 1% sodium chlorite for 18 hours to inactivate any adsorbed ficin, followed by rinsing in normal saline. The test and control arterial segments were then sleeved with 3.0 mm ePTFE tubes, barbed fittings were attached, and the segments were pressure-fixed with 2.5% glutaraldehyde in 0.2M Sorenson's phosphate buffer (pH 7.0) for 2 hours at 27.6 kPa. After fixation, both segments were rinsed in two changes of sterile saline, and stored at 4° C. in sterile normal saline until required for implantation. The untreated control graft was prepared like the test graft except for the ficin and sodium chlorite steps.

These vessel pairs were implanted into the brachial arteries of 9 adult greyhounds. Each pair was implanted into the brachial arteries of one dog providing a direct comparison of the two treatment within the dog. The graft pairs, 2.5 cm in length, were implanted using standard end-to-end surgical technique. Each dog received sodium heparin at 150 U/kg before the first artery was clamped. Following implantation, the total heparin dose was reversed with protamine sulfate. At two weeks postoperatively, each pair of brachial implants was surgically exposed and the patency tested by transecting the artery distal to the implant location. The ficin-treated test grafts were patent in zero of nine (0/9) cases while the untreated control grafts were patent in five of nine (5/9) cases. Thus, enzymatic treatment of the vessel produced a negative effect that destroyed patency.

Example 10

In some situations, it is desirable to reduce the outside diameter of a donor blood vessel. This example illustrates a processing step using proteolytic enzymes to digest the outer tissue layers of a donor blood vessel to reduce the outer diameter of the vessel in order to provide for a thin-walled graft that would have better handling characteristics, while retaining the improved patency performance of a preserved subendothelial matrix layer of the present invention.

Distal cow limbs were obtained at slaughter and stored frozen at –20° C. until processed. After thawing by immersing the legs in warm water, the median arteries (front limb) and the dorsal metatarsal arteries (hind limb) were dissected free and rinsed of blood in HBSS. The arteries were arbitrarily placed in a control group and an inventive group. The adventitia was removed from the arteries by dissection and side branches were ligated. Endothelial cells were removed from the luminal surface of the arteries with flowing air for about five (5) minutes, followed by a brief rinsing in HBSS. Control arteries were placed into 0.2M Tris buffer, pH 7.5, and incubated at 37° C. for about 6 hours. Inventive arteries were filled with ethylenediamine tetraacetic acid (EDTA; 5 mg/ml) in calcium-magnesium-free HBSS, the ends were sealed, and the arteries immersed in 0.2M Tris buffer, pH 7.5, containing 33 units/ml collagenase. The inventive arteries were then incubated in the collagenase solution at 37° C. for about 6 hours. The effect of this treatment was to enzymatically remove the adventitia and portions of the media from the artery, leaving the subendothelial matrix layer intact. After incubation, both control and inventive arteries were rinsed in HBSS, mounted on barbed syringe fittings, and sleeved with a 3.5 mm GORE-TEX® Vascular Graft. (W. L. Gore & Associates, Inc., Flagstaff, Ariz.) The arteries were pressure fixed at about 27.6 kPa for 2 hours using 2.5% glutaraldehyde in 0.2M Sorenson's phosphate buffer, pH 7.0–7.5, resulting in a finished graft of about 2–3 mm internal diameter. After fixation, the arteries were rinsed in sterile normal saline and stored in sterile normal saline at 4° C. until use. The arteries were each implanted with the GORE-TEX® Vascular Graft sleeve in place.

Using standard end-to-end surgical technique, one control and one test graft were implanted as test pairs into the brachial arteries of six (6) greyhound dogs so that a direct comparison of graft function within the dogs could be compared. At 2 weeks postoperatively, three of six (3/6) inventive, collagenase-treated, arteries were patent and two of six (2/6) control, mock digested, arteries were patent. Thus, removal of the artery media with collagenase does not compromise patency as long as the subendothelial matrix layer is protected from the collagenase and subsequently preserved.

Example 11

In one embodiment of the present invention, the subendothelial matrix layer is removed from a donor blood vessel and applied to the surface of an artificial vascular prosthesis made of synthetic materials and preserved. This example illustrates the patency performance of such a prosthesis.

A commercially available 4 mm GORE-TEX® Vascular Graft (W. L. Gore & Associates, Inc., Flagstaff, Ariz.) was modified through the addition of subendothelial matrix layer derived from a donor cow aorta. The donor vessel was obtained at slaughter and frozen until use in the manner previously described in Example 2. After opening with a longitudinal incision, the intimal surface was gently rubbed with a paper towel to ensure removal of endothelial cells remaining after the freezing-thawing cycle. Then, using a scalpel blade, the intimal surface of the donor vessel was carefully scraped, taking care to not penetrate the internal elastic lamina. The subendothelial matrix derived in this manner from approximately 5.0 cm of cow aorta was used for a single 4.0 mm×5.0 cm inventive graft. The scrapings from the cow aorta were suspended in about 50 ml HBSS and subjected to homogenization with a Verti-shear mixer for about 60 seconds. The homogenized subendothelial matrix layer was allowed to sit for about 10 minutes to allow the larger clumps to settle out and the remainder of the homogenate decanted. The suspension was placed in a syringe until ready for use. A GORE-TEX® Vascular Graft (W. L. Gore & Associates, Inc., Flagstaff, Ariz.) was mounted on barbed fittings. The ePTFE vascular graft was wetted with 100% ethanol and the ethanol displaced with HBSS. An aliquot from the syringe containing the subendothelial matrix layer scrapings was then forced through the pores of the graft, depositing the subendothelial matrix on the surface of the graft. The graft was then soaked in a 2.5% glutaraldehyde solution for two hours to preserve the subendothelial matrix layer and to assure sterility. The graft was rinsed in multiple sterile saline changes, and stored in sterile saline at 4° C. until implantation.

This inventive graft was implanted into the carotid artery of an adult greyhound. The 4.0 mm internal diameter graft was a good diameter match to the native carotid artery of the dog and standard end-to-end surgical technique was used for implantation. No antiplatelet agents were administered to the dog at any time and 100 U/kg heparin was administered only during the intraoperative phase. The course of the implant was followed using contrast angiography and duplex ultrasound examination. At one month implant duration, the inventive graft was surgically exposed and tested for patency by transecting the artery distal to the implant location. The inventive graft was found to be patent.

Example 12

This example illustrates -the discovery that an ammonium hydroxide treatment of the lumen of de-endothelialized allogeneic arteries, prior to preserving the subendothelial matrix layer, shows improved patency compared to arteries not treated with ammonium hydroxide.

Pairs of carotid artery segments were removed from donor greyhound dogs, placed into vials containing 15% DMSO in HBSS, and stored frozen under liquid nitrogen until subsequent processing. At processing, each vial was immersed in a water bath at 37° C. until thawed. Each pair of arteries was removed from the vial, rinsed in normal saline, and the adventitia removed by manual dissection. The vessels were mounted on barbed fittings using 3-0 silk suture and placed inside a thin walled 3.0 mm GORE-TEX® Vascular Graft (W. L. Gore & Associates, Inc., Flagstaff, Ariz.) sleeves to provide a finished internal diameter of about 2.5 mm.

Both vessels of each pair were then exposed to flowing air (about 1000 cc/min) for 5 minutes to remove any endothelium remaining after the above freeze-storage-thaw cycle and again flushed with HBSS. Scanning electron microscopy (SEM) inspection of representative samples of artery subjected to flowing air confirmed near total loss, for example, greater than 80%, of the native endothelium and the maintenance of the subendothelial matrix layer. One artery of each pair was then selected for NH$_4$OH treatment and served as the inventive graft. Each of these inventive grafts was placed in a 0.25M solution of NH$_4$OH for one hour. The other artery of each pair was selected to serve as the control graft, and was similarly processed but without the NH$_4$OH treatment step.

The vessel pairs were again rinsed with HBSS, immersed in 2.5% glutaraldehyde in 0.2M Sorenson's phosphate buffer (pH 7.0–7.2), and the solution forced into the lumen at 27.6 kPa pressure for 2 hours. Using sterile technique, the ePTFE sleeves were then removed, the ends of the artery segments trimmed, the vessels rinsed thoroughly in sterile normal saline and stored in sterile normal saline at 4° C. until implantation.

These control and inventive grafts were implanted as test pairs into the brachial arteries of 9 adult greyhounds dogs. Each pair was implanted into the brachial arteries of the same dog so that a direct comparison of the vessels within each dog was achieved. The vessel grafts, 2.5 cm long with an internal diameter of 2.5 mm, were a good diameter match to the native brachial artery of the adult greyhound recipients. Standard end-to-end surgical technique was used for implantation and no anticoagulants or antiplatelet agents were administered to the dogs at any time. Each dog was followed daily for the first two weeks using a doppler ultrasound duplex scanner, and weekly thereafter. Contrast angiography was also periodically employed to confirm patency status.

At two months postoperatively, the NH$_4$OH treated inventive graft was confirmed to be patent in four of nine (4/9) cases, while the control, non-treated grafts were patent in one of nine (1/9) cases. In conclusion, the inventive graft demonstrates that the NH$_4$OH treatment provides improved patency in allogeneic artery transplants compared to non-treated allogeneic control vessels although in both cases the donor endothelium was removed.

Example 13

This example illustrates the discovery that a chloroform and methanol treatment of de-endothelialized donor arteries, prior to preserving the subendothelial matrix layer, shows improved patency compared to arteries not treated with chloroform and methanol.

Bovine leg segments were obtained at slaughter and stored frozen at −20° C. until processing. After thawing by immersing the legs in warm water, the median arteries (front limb) and the dorsal metatarsal arteries (hind limb), were dissected free and rinsed of blood in HBSS. Segments of artery having an internal diameter of about 2–3 mm were identified, the adventitia removed by dissection, the branches tied, and the vessel segments mounted on barbed fittings. To ensure the absence of donor endothelium, the lumen of each vessel segment was air dried with flowing air at about 1000 cc/min for about 5 minutes, followed by a brief flush with HBSS. Half of the segment was arbitrarily designated as the inventive graft and half as the control graft. The inventive grafts were then immersed in a solution of chloroform and methanol (CHCl$_3$/CH$_3$OH;2:1 V:V) for about 30 minutes at room temperature. The solvent was allowed to evaporate from the inventive grafts and the grafts rehydrated in normal saline for about 30 minutes. The vessels were then sleeved in commercially available 3.0 mm thin walled GORE-TEX® Vascular Graft (W. L. Gore & Associates, Inc., Flagstaff, Ariz.) to provide a finished internal diameter of about 2.5 mm, and perfused with a solution of 2.5% glutaraldehyde in 0.2M Sorenson's phosphate buffer (pH 7.0) for 2 hours at 27.6 kPa. After fixing, the sleeves were removed, the ends of the vessel segments trimmed, and the segments rinsed in two 500 ml changes of sterile saline for a total of 30 minutes to remove residual glutaraldehyde. The treated artery segments were stored in sterile normal saline at 4° C. until implantation. The control artery segments were similarly processed except that they were not subjected to the CHCl$_3$/CH$_3$OH extraction.

The inventive and control grafts were implanted as a test pair into the brachial arteries of 8 adult greyhound dogs with one brachial artery of each dog receiving the inventive extracted graft and the contralateral artery receiving the non-extracted control graft. The grafts, 2.5 cm in length, were implanted using standard end-to-end surgical technique. No anti-coagulants or antiplatelet agents were administered at any time. Each dog was followed daily for the first two weeks using a doppler ultrasound duplex scanner, and weekly thereafter. Contrast angiography was also periodically employed to confirm patency status. At one month postoperatively, the inventive grafts that had been subjected to the CHCl$_3$/CH$_3$OH extraction were confirmed to be patent in five of eight (5/8) cases, while the control grafts were patent in one of eight (1/8) cases. Thus, the chloroform and methanol treatment resulted in improved patency of the inventive grafts compared to controls.

Example 14

This example demonstrates improved patency with the chloroform and methanol treatment described above in Example 13, using donor arteries with a finished internal diameter of 4.0 mm, compared to the 2.5 mm finished internal diameter of the grafts described in Example 13.

Distal leg arteries, 4–5 mm diameter, were obtained from cows and processed as described in Example 13, except that they were pressure fixed with glutaraldehyde inside a 5.0 mm sleeve tube to provide a finished internal diameter of about 4.0 mm. Again, the inventive and control segments were identically processed with the exception of the chloroform and methanol extraction step.

Using standard end-to-end surgical technique, 4.0 cm lengths of both grafts were implanted as test pairs into the femoral arteries of 7 adult greyhound dogs. One femoral artery of each dog was implanted with the non-extracted control graft and the contralateral artery received an inventive extracted graft. No anticoagulants or antiplatelet agents were administered at any time. Each dog was followed daily for the first two weeks using a doppler ultrasound duplex scanner, and weekly thereafter. Contrast angiography was also employed to determine patency status in the event of questionable ultrasound results. At one month, the extracted inventive grafts were patent in five of seven (5/7) cases while the non-extracted control grafts were patent in two of seven (2/7) cases. As in Example 13, the extraction with the $CHCl_3/CH_3OH$ organic solvent resulted in improved patency.

Example 15

The following example illustrates the performance of pig arteries used as arterial implants in dogs in two separate experiments. In the first experiment, one set of test de-endothelialized pig arteries was processed only with glutaraldehyde treatment. In the second experiment, another set of inventive de-endothelialized pig arteries was processed according to the present invention as described above in Examples 12 and 13, followed by the glutaraldehyde treatment employed in the first experiment of this example. In the two experiments, both sets of pig arteries were compared to an ePTFE graft of the same diameter.

In the first experiment, segments of carotid artery, approximately 2-3 mm in internal diameter, were obtained from pigs, placed in vials of 15% DMSO in HBSS and frozen at −70° C. until processing. After thawing by immersion in warm water, the adventitia of each vessel was removed by dissection. Each segment was inserted into a 3.0 mm sleeve to provide a finished fixed internal diameter of about 2.5 mm. The vessels, contained in the external sleeves, were mounted on barbed fittings. To ensure the absence of donor endothelium following the above freeze-storage-thaw cycle, the lumen of each vessel segment was air dried with flowing air at about 1000 cc/min for about 5 minutes, followed by a brief flush with HBSS.

The vessels were perfused with a solution of 0.25% (V:V) glutaraldehyde in 20 mM HEPES containing 4.4 g/liter NaCl and 2.6 g/liter of $MgCl_2.6H_2O$ for 2 hours at 27.6 kPa. After pressure fixing, the sleeves were removed, and the test grafts placed in the 0.25% glutaraldehyde solution an additional 8-24 hours. Upon removal from the glutaraldehyde treatment, the grafts were extensively rinsed and stored in normal saline at 4° C. for at least 24 hours. Before surgical insertion, each graft was changed to a saline solution containing 30 U/ml heparin for at least 8 hours.

At implant, each processed test porcine artery graft was trimmed to 2.5 cm in length. One of these grafts was implanted into one brachial artery of 7 adult greyhound dogs. In the contralateral brachial artery of each dog, a control graft was implanted. The control graft was a 2.5 cm length of 2.5 mm ePTFE tubing, described in Example 3. Thus, the two graft types were implanted as a test pair in a single dog. The grafts were implanted using standard end-to-end surgical technique. No anti-coagulants or antiplatelet agents were administered at any time. Each dog was followed daily for the first two weeks using a doppler ultrasound duplex scanner, and weekly thereafter. Contrast angiography was also periodically employed to confirm patency status. At one month postoperatively, the processed porcine grafts were patent in one of seven (1/7) cases while the control ePTFE grafts were patent in zero of seven (0/7) cases.

In the second experiment of this example, the porcine arteries were processed in a manner similar to that of the first experiment, but were additionally subjected to the inventive processes previously described above in Examples 12 and 13, respectively. Each of the inventive porcine grafts were initially stored in vials of 15% DMSO in HBSS and stored frozen under liquid nitrogen until processing. After removal of the adventitia, each graft was placed in a 0.25M solution of $NH_4OH$ for about 3 minutes and rinsed in HBSS as described in Example 12. As in Example 13, the inventive graft was then immersed in a solution of chloroform and methanol ($CHCl_3/CH_3OH$; 2:1 V:V) for about 30 minutes at room temperature. After the residual chloroform and methanol solvent evaporated from the grafts, each extracted graft was then rehydrated in HBSS for about 30 minutes, and placed inside a 3.0 mm diameter sleeve to provide a finished diameter of about 2.5 mm following fixation. The vessels were then perfused with a solution of 0.25% (V:V) glutaraldehyde in 20 mM HEPES buffer with 4.4 g/liter NaCl and 2.6 g/liter $MgCl_2.6H_2O$ for 2 hours at 27.6 kPa. After pressure fixing, the sleeve was removed, and the grafts placed in the 0.25% glutaraldehyde solution an additional 8-24 hours. As in the first experiment of this example, the grafts were extensively rinsed and stored in normal saline at 4° C. for at least 24 hours, then changed to a saline solution containing 30 U/ml heparin for at least 8 hours.

As in the first experiment of this example, the inventive porcine graft was implanted in comparison to a control ePTFE graft as a test pair in adult greyhound dogs. Brachial pair comparisons were conducted in seven animals. Each dog was again followed with a doppler ultrasound duplex scanner, and weekly contrast angiography. At one month post-implantation, the inventive porcine grafts were patent in four of seven (4/7) cases, while the control ePTFE grafts were patent in one of seven (1/7) cases. This example serves to illustrate the incremental patency performance provided by the process of the present invention.

While particular embodiments of the present invention have been illustrated and described herein, the present invention should not be limited to such illustrations and descriptions. It should be apparent that changes and modifications may be incorporated and embodied as part of the present invention within the scope of the claims.

TABLE 1

Summary of Example Tests and Patency Results

| EXAMPLE | GRAFT TYPE | DIAMETER* (mm) | IMPLANT TIME (days) | PATENCY RESULTS | PATENCY % |
|---|---|---|---|---|---|
| 1 | Inventive | 2.5 | 14 | 6/6 | 100 |
| 1 | Control | 2.5 | 14 | 1/6 | 17 |
| 2 | Inventive | 2.5 | 393 | 1/1 | 100 |
| 2 | Control | 2.5 | 393 | 1/1 | 100 |
| 3 | Inventive | 2.5 | 30 | 3/5 | 60 |
| 3 | Control | 2.5 | 30 | 1/5 | 20 |
| 4 | Inventive | 5.0 | 30 | 3/6 | 50 |

TABLE 1-continued

Summary of Example Tests and Patency Results

| EXAMPLE | GRAFT TYPE | DIAMETER* (mm) | IMPLANT TIME (days) | PATENCY RESULTS | PATENCY % |
|---|---|---|---|---|---|
| 4 | Control | 5.0 | 30 | 0/6 | 0 |
| 5 | Inventive | 2.5 | 30 | 1/1 | 100 |
| 5 | Control | 2.5 | 30 | 0/1 | 0 |
| 6 | Inventive | 4.0 | 30 | 4/4 | 100 |
| 6 | Control | 4.0 | 30 | 2/4 | 50 |
| 7 | Test | 2.5 | 21 | 0/7 | 0 |
| 7 | Control | 2.5 | 21 | 5/7 | 71 |
| 8 | Test | 2.5 | 90 | 1/5 | 20 |
| 8 | Control | 2.5 | 90 | 4/5 | 80 |
| 9 | Test | 2.5 | 14 | 0/9 | 0 |
| 9 | Control | 2.5 | 14 | 5/9 | 56 |
| 10 | Inventive | 2.5 | 14 | 3/6 | 50 |
| 10 | Control | 2.5 | 14 | 2/6 | 33 |
| 11 | Inventive | 4.0 | 30 | 1/1 | 100 |
| 11 | — | — | — | — | — |
| 12 | Inventive | 2.5 | 60 | 4/9 | 44 |
| 12 | Control | 2.5 | 60 | 1/9 | 11 |
| 13 | Inventive | 2.5 | 30 | 5/8 | 63 |
| 13 | Control | 2.5 | 30 | 1/8 | 13 |
| 14 | Inventive | 4.0 | 30 | 5/7 | 71 |
| 14 | Control | 4.0 | 30 | 2/7 | 29 |
| 15a | Test | 2.5 | 30 | 1/7 | 14 |
| 15a | Control | 2.5 | 30 | 0/7 | 0 |
| 15b | Inventive | 2.5 | 30 | 4/7 | 57 |
| 15b | Control | 2.5 | 30 | 1/7 | 14 |

*Graft lengths for 2.5, 4.0, and 5.0 mm diameter grafts are 2.5, 4.0, and 5.0 cm, respectively.

The invention claimed is:

1. A method of producing a blood contact surface which comprises:
   providing a donor blood vessel, including endothelial cells attached to a subendothelial matrix layer;
   treating the donor blood vessel so as to remove the endothelial cells while leaving the subendothelial matrix layer in situ;
   treating the donor blood vessel with a proteolytic enzyme to reduce the outer diameter of the blood vessel, while protecting the subendothelial matrix layer from the proteolytic enzyme;
   treating the donor blood vessel to preserve the subendothelial matrix layer in situ; and
   employing the subendothelial matrix layer as a direct blood contact surface in an appliance.

2. The method of claim 1 which further comprises:
   surrounding the donor blood vessel with a sheath comprised of a material that permits the passage of macromolecules across the thickness of the sheath to and from the blood vessel while resisting ingrowth of cells from tissues surrounding the blood vessel when implanted.

3. The method of claim 1 which further comprises:
   eating the donor blood vessel to prevent calcification with a solution of chloroform and methanol.

4. The method of claim 1 wherein the proteolytic enzyme is selected from at least one member of a group consisting of collagenase, papain, trypsin, chymotrypsin, and elastase.

5. A method of producing a blood contact surface which comprises:
   providing a donor blood vessel, including endothelial cells attached to a subendothelial matrix layer, having an exterior surface and an interior surface;
   treating the donor blood vessel so as to remove the endothelial cells while leaving the subendothelial matrix layer in situ;
   treating the donor blood vessel to preserve the subendothelial matrix layer in situ;
   surrounding the exterior surface of the donor blood vessel with a sheath comprised of a material that permits the passage of macromolecules across the thickness of the sheath to and from the blood vessel while resisting ingrowth of cells from tissues surrounding the blood vessel when implanted; and
   employing the subendothelial matrix layer as a direct blood contact surface in an appliance comprising an artificial blood vessel.

6. The method of claim 5 which further comprises:
   treating the donor blood vessel to prevent calcification with a solution of chloroform and methanol.

7. A process of producing a direct blood contact surface on an artificial blood vessel which comprises:
   providing a natural blood contact surface derived from a donor blood vessel, including an endothelial cell layer attached to a subendothelial matrix layer;
   stripping the endothelial cell layer from the subendothelial matrix layer so as to leave the subendothelial matrix layer in situ;
   treating the blood contact surface to preserve the subendothelial matrix layer in situ;
   surrounding the donor blood vessel with a sheath comprising a porous polytetrafluoroethylene material that is permeable to macromolecules but resistant to cell ingrowth; and
   employing the preserved subendothelial matrix layer substantially free of endothelial cells as a direct blood contact surface.

8. The process of claim 7 which further comprises:
   treating the donor blood vessel to prevent calcification with a solution of chloroform and methanol.

9. A process of producing a direct blood contact surface which comprises:
   providing a natural blood contact surface derived from a donor blood vessel, including an endothelial cell layer attached to a subendothelial matrix layer;
   stripping the endothelial cell layer from the subendothelial matrix layer so as to leave the subendothelial matrix layer in situ;
   treating the donor blood vessel to reduce the outer diameter of the blood vessel with a proteolytic enzyme, while protecting the subendothelial matrix layer from the proteolytic enzyme;
   treating the blood contact surface to preserve the subendothelial matrix layer in situ; and
   employing the preserved subendothelial matrix layer substantially free of endothelial cells as a direct blood contact surface.

10. The process of claim 9 which further comprises:
    surrounding the donor blood vessel with a sheath comprised of a material that permits the passage of macromolecules across the thickness of the sheath to and from the blood vessel while resisting ingrowth of cells from tissues surrounding the blood vessel when implanted.

11. The process of claim 9 which further comprises:
    treating the donor blood vessel to prevent calcification with a solution of chloroform and methanol.

12. The process of claim 9 wherein the proteolytic enzyme is selected from at least one member of a group consisting of collagenase, papain, trypsin, chymotrypsin, and elastase.

13. A method of producing a direct blood contact surface with improved patency performance which comprises:
   providing a natural blood contact surface derived from a donor, including an endothelial cell layer attached to a subendothelial matrix layer;
   stripping the endothelial cell layer from the subendothelial matrix layer so as to leave the subendothelial matrix layer in situ;
   treating the subendothelial matrix layer with a solution of ammonium hydroxide to improve patency;
   treating the subendothelial matrix layer to preserve the subendothelial matrix layer; and
   employing the preserved subendothelial matrix layer substantially free of endothelial cells as a direct blood contact surface.

14. The method of claim 13 which further comprises:
   surrounding the blood contact surface with a sheath comprised of a material that permits the passage of macromolecules across the thickness of the sheath to and from the blood contact surface while resisting ingrowth of cells from tissues surrounding the blood contact surface when implanted.

15. The method of claim 13 which further comprises:
   treating the blood contact surface to prevent calcification with a solution of chloroform and methanol.

16. The method of claim 13 which further comprises:
   treating the blood contact surface with a proteolytic enzyme to reduce the outer diameter of the blood contact surface of the blood contact surface, while protecting the subendothelial matrix layer from the proteolytic enzyme.

17. The method of claim 16 wherein the proteolytic enzyme is selected from at least one member of a group consisting of collagenase, papain, trypsin, chymotrypsin, and elastase.

18. The method of claim 1 wherein the subendothelial matrix layer comprises chondroitin sulfate proteoglycans.

19. The method of claim 18 wherein the subendothelial matrix layer further comprises glycosaminoglycan-bearing proteoglycans.

20. The method of claim 18 wherein the subendothelial matrix layer further comprises fibronectin.

21. The method of claim 19 wherein the subendothelial matrix layer further comprises fibronectin.

22. The method of claim 5 wherein the subendothelial matrix layer comprises chondroitin sulfate proteoglycans.

23. The method of claim 22 wherein the subendothelial matrix layer further comprises glycosaminoglycan-bearing proteoglycans.

24. The method of claim 22 wherein the subendothelial matrix layer further comprises fibronectin.

25. The method of claim 23 wherein the subendothelial matrix layer further comprises fibronectin.

26. The method of claim 7 wherein the subendothelial matrix layer comprises chondroitin sulfate proteoglycans.

27. The method of claim 26 wherein the subendothelial matrix layer further comprises glycosaminoglycan-bearing proteoglycans.

28. The method of claim 26 wherein the subendothelial matrix layer further comprises fibronectin.

29. The method of claim 27 wherein the subendothelial matrix layer further comprises fibronectin.

30. The method of claim 9 wherein the subendothelial matrix layer comprises chondroitin sulfate proteoglycans.

31. The method of claim 30 wherein the subendothelial matrix layer further comprises glycosaminoglycan-bearing proteoglycans.

32. The method of claim 30 wherein the subendothelial matrix layer further comprises fibronectin.

33. The method of claim 31 wherein the subendothelial matrix layer further comprises fibronectin.

34. The method of claim 13 wherein the subendothelial matrix layer comprises chondroitin sulfate proteoglycans.

35. The method of claim 34 wherein the subendothelial matrix layer further comprises glycosaminoglycan-bearing proteoglycans.

36. The method of claim 34 wherein the subendothelial matrix layer further comprises fibronectin.

37. The method of claim 35 wherein the subendothelial matrix layer further comprises fibronectin.

38. A method of producing a blood contact surface which comprises:
   providing a donor blood vessel, including endothelial cells attached to a subendothelial matrix layer;
   treating the donor blood vessel so as to remove only the endothelial cells while leaving the subendothelial matrix layer in situ;
   treating the donor blood vessel to preserve the subendothelial matrix layer;
   treating the donor blood vessel with a proteolytic enzyme to reduce the outer diameter of the blood vessel, while protecting the subendothelial matrix layer from the proteolytic enzyme; and
   employing the subendothelial matrix layer as a direct blood contact surface in an appliance.

39. The method of claim 38 wherein the subendothelial matrix layer comprises chondroitin sulfate proteoglycans.

40. The method of claim 39 wherein the subendothelial matrix layer further comprises glycosaminoglycan-bearing proteoglycans.

41. The method of claim 39 wherein the subendothelial matrix layer further comprises fibronectin.

42. The method of claim 40 wherein the subendothelial matrix layer further comprises fibronectin.

43. A method of producing a blood contact surface which comprises:
   providing a donor blood vessel, including endothelial cells attached to a subendothelial matrix layer;
   treating the donor blood vessel so as to remove only the endothelial cells while leaving the subendothelial matrix layer in situ;
   treating the donor blood vessel to preserve the subendothelial matrix layer;
   employing the subendothelial matrix layer as a direct blood contact surface in an appliance, wherein the appliance comprises an artificial blood vessel having an exterior surface and an interior surface; and
   surrounding the exterior surface of the donor blood vessel with a sheath, wherein the sheath comprises a material which permits the passage of macromolecules across the thickness of the sheath to and from the donor blood vessel while resisting ingrowth of cells from tissue surrounding the donor blood vessel when implanted.

44. The method of claim 43 wherein the subendothelial matrix layer comprises chondroitin sulfate proteoglycans.

45. The method of claim 44 wherein the subendothelial matrix layer further comprises glycosaminoglycan-bearing proteoglycans.

46. The method of claim 44 wherein the subendothelial matrix layer further comprises fibronectin.

47. The method of claim 45 wherein the subendothelial matrix layer further comprises fibronectin.

48. A process of producing a direct blood contact surface which comprises:

provding a natural blood contact surface derived from a donor blood vessel, including an endothelial cell layer attached to a subendothelial matrix layer;

stripping only the endothelial cell layer from the subendothelial matrix layer so as to leave the subendothelial matrix layer in situ;

treating the blood contact surface to preserve the subendothelial matrix layer;

surrounding the donor blood vessel with a sheath comprised of a porous polytetrafluoroethylene material that is permeable to macromolecules, but resistant to cell ingrowth; and employing the preserved subendothelial matrix layer substantially free of endothelial cells as a direct blood contact surface.

49. The method of claim 48 wherein the subendothelial matrix layer comprises chondroitin sulfate proteoglycans.

50. The method of claim 49 wherein the subendothelial matrix layer further comprises glycosaminoglycan-bearing proteoglycans.

51. The method of claim 49 wherein the subendothelial matrix layer further comprises fibronectin.

52. The method of claim 50 wherein the subendothelial matrix layer further comprises fibronectin.

53. A process of producing a direct blood contact surface which comprises:

providing a natural blood contact surface derived from a donor blood vessel, including an endothelial cell layer attached to a subendothelial matrix layer;

stripping only the endothelial cell layer from the subendothelial matrix layer so as to leave the subendothelial matrix layer in situ;

treating the blood contact surface to preserve the subendothelial matrix layer;

treating the donor blood vessel with a proteolytic enzyme to reduce the outer diameter of the blood vessel, while protecting the subendothelial matrix layer from the proteolytic enzyme; and employing the preserved subendothelial matrix layer substantially free of endothelial cells as a direct blood contact surface.

54. The method of claim 53 wherein the subendothelial matrix layer comprises chondroitin sulfate proteoglycans.

55. The method of claim 54 wherein the subendothelial matrix layer further comprises glycosaminoglycan-bearing proteoglycans.

56. The method of claim 54 wherein the subendothelial matrix layer further comprises fibronectin.

57. The method of claim 55 wherein the subendothelial matrix layer further comprises fibronectin.

58. A process of producing a direct blood contact surface which comprises:

providing a natural blood contact surface derived from a donor blood vessel, including an endothelial cell layer attached to a subendothelial matrix layer;

stripping only the endothelial cell layer from the subendothelial matrix layer so as to leave the subendothelial matrix layer in situ;

treating the blood contact surface to preserve the subendothelial matrix layer;

treating the donor blood vessel with a proteolytic enzyme to reduce the outer diameter of the blood vessel, while protecting the subendothelial matrix layer from the proteolytic enzyme, wherein the proteolytic enzyme selected from at least one member of a group consisting of collagenase, papain, trypsin, chymotrypsin, and elastase; and employing the preserved subendothelial matrix layer substantially free of endothelial cells as a direct blood contact surface.

59. The method of claim 58 wherein the subendothelial matrix layer comprises chondroitin sulfate proteoglycans.

60. The method of claim 59 wherein the subendothelial matrix layer further comprises glycosaminoglycan-bearing proteoglycans.

61. The method of claim 59 wherein the subendothelial matrix layer further comprises fibronectin.

62. The method of claim 60 wherein the subendothelial matrix layer further comprises fibronectin.

* * * * *